United States Patent [19]

Kosley, Jr. et al.

[11] Patent Number: 5,104,985

[45] Date of Patent: Apr. 14, 1992

[54] LABDANE PROCESS

[75] Inventors: Raymond W. Kosley, Jr., Bridgewater; Robert J. Cherill, Somerset, both of N.J.

[73] Assignee: Hoechst-Roussel Pharmaceuticals Inc., Somerville, N.J.

[21] Appl. No.: 705,821

[22] Filed: May 28, 1991

Related U.S. Application Data

[60] Division of Ser. No. 410,834, Sep. 21, 1989, which is a continuation of Ser. No. 106,305, Oct. 9, 1987, abandoned, which is a continuation of Ser. No. 921,663, Oct. 20, 1986, abandoned, which is a division of Ser. No. 848,053, Apr. 14, 1986, Pat. No. 4,639,443, which is a continuation-in-part of Ser. No. 707,283, Mar. 1, 1985, abandoned.

[51] Int. Cl.$^5$ ................ C07D 417/02; C07D 417/12; C07D 311/92

[52] U.S. Cl. .................... 544/57; 544/58.7; 544/145; 544/148; 544/150; 544/375; 546/22; 546/196; 546/197; 548/413; 548/525; 548/526; 549/5; 549/25; 549/220; 549/377; 549/384; 549/389

[58] Field of Search ............ 544/57, 58.7, 145, 148, 544/150, 375; 546/22, 196, 197; 548/413, 525, 526; 549/5, 25, 220, 377, 384, 389

[56] References Cited

U.S. PATENT DOCUMENTS 4,639,446  1/1987  Kosley, Jr. .................. 549/389

OTHER PUBLICATIONS

S. V. Bhat, et al., J.C.S. Perkin I, 767 (1982).
S. V. Bhat, et al., Tetrahedron Letters, 1669 (1977).

Primary Examiner—Robert W. Ramsuer
Attorney, Agent, or Firm—Raymond R. Wittekind

[57] ABSTRACT

Novel labdanes, intermediates and processes for the preparation thereof, and methods for reducing intraocular pressure utilizing compounds or compositions thereof are disclosed.

5 Claims, No Drawings

LABDANE PROCESS

This is a division of application Ser. No. 410,834 filed Sept. 21, 1989, which is a continuation of application Ser. No. 106,305 filed Oct. 9, 1987 now abandoned, which is a continuation of application Ser. No. 921,663 filed Oct. 20, 1986 now abandoned, which is a divisional of application Ser. No. 848,053 filed Apr. 14, 1986 now U.S. Pat. No. 4,639,443, which is a continuation-in-part of application Ser. No. 707,283 filed Mar. 1, 1985 now abandoned.

The present invention relates to labdanes. More particularly, the present invention relates to labdanes of formula 1

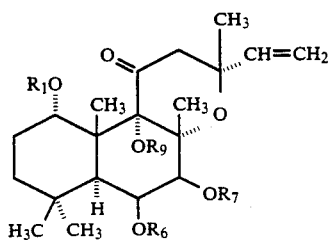

1 wherein (a) $R_1$ is hydrogen, a group of the formula $R_3R_4R_5Si$ wherein $R_3$, $R_4$ and $R_5$ are each independently loweralkyl, a group of the formula $R_2CO$ wherein $R_2$ is hydrogen, loweralkyl, or a group of the formula $R_{24}R_{25}NCHR_{26}$ wherein $R_{24}$ is hydrogen, loweralkyl or benzyl, $R_{25}$ is hydrogen or loweralkyl and $R_{26}$ is hydrogen, loweralkyl or benzyl; $R_{24}$ and $R_{25}$ taken together with the nitrogen atom to which they are attached form a group of formula

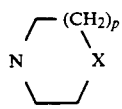

wherein X is O, S or a group of the formula $CHR_{27}$ wherein $R_{27}$ is hydrogen, loweralkyl or a group of the formula $OR_{28}$ wherein $R_{28}$ is hydrogen, loweralkyl or a group of the formula $COR_{29}$ wherein $R_{29}$ is loweralkyl and p is 0 or 1;

(b) $R_6$ and $R_7$ are each independently hydrogen, a group of the formula $R_8CO$ wherein $R_8$ is hydrogen, loweralkyl,

$CH_3CHOH$, $HOCH_2CHOH$, $(CH_3)_2COCH_2OCH_2CH_2OCH_3$, $CH_3C(CH_3)OH$, $HOCH_2C(CH_3)OH$, $HOCH_2C(CH_3)_2$, $CH_3C(CH_2OH)_2$, $C(CH_2OH)_3$, $HOC(CH_2OH)CH_2CH_3$,

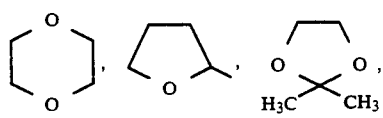

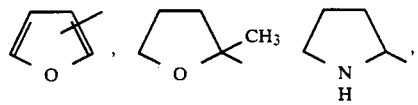

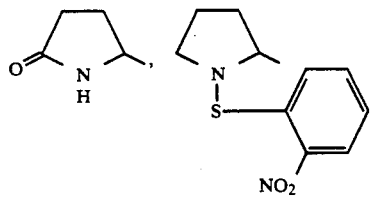

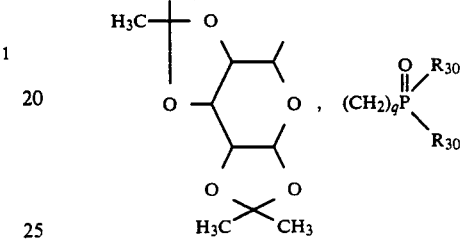

Wherein $R_{30}$ is loweralkyl and q is 1, 2 or 3, a group of the formula $R_{10}OCR_{31}R_{32}(CH_2)_n$ wherein $R_{10}$ is hydrogen or loweralkyl, $R_{31}$ is hydrogen or loweralkyl, $R_{32}$ is hydrogen or loweralkyl and n is 0, 1, 2 or 3, a group of the formula $R_{11}R_{12}NCHR_{13}$ wherien $R_{11}$ is hydrogen, loweralkyl, a group of the formula

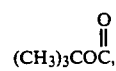

a group of the formula

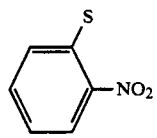

or a group of the formula $R_{14}CO$ wherein $R_{14}$ is hydrogen or loweralkyl; $R_{12}$ is hydrogen or loweralkyl; $R_{13}$ is hydrogen, loweralkyl, benzyl or a group of the formula $CH_2OH$; $R_{11}$ and $R_{12}$ taken together with the nitrogen atom to which they are attached form a group of the formula

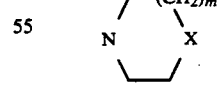

wherein X is O, S or a group of the formula $CHR_{15}$ wherein $R_{15}$ is hydrogen, loweralkyl or a group of the formula $OR_{16}$ wherein $R_{16}$ is hydrogen, loweralkyl or a group of the formula $COR_{17}$ wherein $R_{17}$ is loweralkyl and m is 0 or 1; a group of the formula $NR_{18}$ wherein $R_{18}$ is loweralkyl; and $R_6$ and $R_7$ taken together form a group of the formula CO or a group of the formula SO;

(c) $R_9$ is hydrogen;

(d) $R_1$ and $R_9$ taken together form a group of the formula CO, a group of the formula SO or a group of the formula $CHNR_{19}R_{20}$ wherein $R_{19}$ and $R_{20}$ are each independently loweralkyl; and $R_{19}$ and $R_{20}$ taken together with the nitrogen atom to which they are attached form a group of the formula

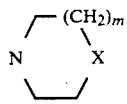

wherein X and m are as hereinbeforedescribed; with the provisos:

(e) that $R_6$ is not hydrogen or $R_8CO$ wherein $R_8$ is hydrogen or loweralkyl when $R_7$ is hydrogen or $R_8CO$ wherein $R_8$ is hydrogen or loweralkyl; $R_1$ is hydrogen, $R_2CO$ or $R_3R_4R_5Si$ wherein $R_3,R_4$ and $R_5$ are as above; and $R_9$ is hydrogen;

(f) that $R_1$ is not hydrogen or $R_2CO$ when $R_9$ is hydrogen and $R_6$ and $R_7$ taken together are CO;

(g) that $R_1$ and $R_9$ taken together are not CO or SO when $R_6$ is hydrogen or $R_8CO$ wherein $R_8$ is hydrogen or loweralkyl; and $R_7$ is hydrogen or $R_8CO$ wherein $R_8$ is hydrogen or loweralkyl; or when $R_6$ and $R_7$ taken together are CO or SO; the optical and geometric isomers thereof, or a pharmaceutically acceptable acid addition salt thereof, which are useful for reducing intraocular pressure, alone or in combination with inert adjuvants.

Subgeneric to the labdanes of the present invention are compounds of formula 1 wherein:

(a) $R_1$ and $R_9$ are hydrogen and $R_6$ is a group of the formula $R_8CO$ wherein $R_8$ is a group of the formula $R_{11}R_{12}NCHR_{13}$ wherein $R_{11}, R_{12}$ and $R_{13}$ are as hereinbeforedefined;

(b) $R_1$ and $R_9$ are hydrogen and $R_7$ is a group of the formula $R_8CO$ wherein $R_8$ is a group of the formula $R_{11}R_{12}NCHR_{13}$ wherein $R_{11}, R_{12}$ and $R_{13}$ are as hereinbeforedefined;

(c) $R_1$ and $R_9$ are hydrogen and $R_6$ is $R_8CO$ wherein $R_8$ is a group of the formula

$CH_3CHOH$, $HOCH_2CHOH$, $CH_3C(CH_3)OH$, $(CH_3)_2COCH_2OCH_2CH_2OCH_3$,

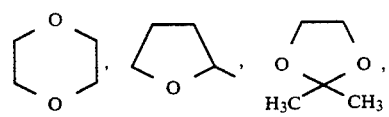

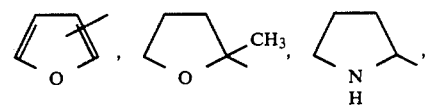

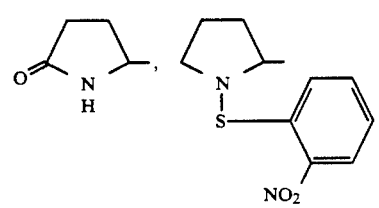

-continued

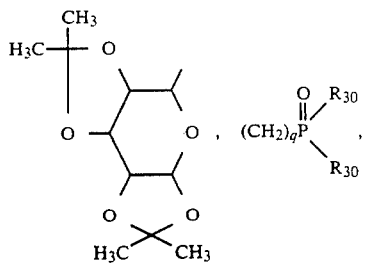

wherien $R_{30}$ is loweralkyl and q is 1, 2 or 3, a group of the formula $R_{10}OCR_{31}R_{32}(CH_2)_n$ wherein $R_{10}$ is hydrogen or loweralkyl, $R_{31}$ is hydrogen or loweralkyl, $R_{32}$ is hydrogen or loweralkyl and n is 0, 1, 2 or 3;

(d) $R_1$ and $R_9$ are hydrogen and $R_7$ is a group of the formula $R_8CO$ wherein $R_8$ is a group of the formula

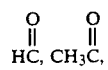

$CH_3CHOH$, $HOCH_2CHOH$, $(CH_3)_2COCH_2OCH_2C-H_2OCH_3$, $CH_3C(CH_3)OH$, $HOCH_2C(CH_3)OH$, $HOCH_2C(CH_3)_2$, $HOC(CH_2OH)CH_2CH_3$.

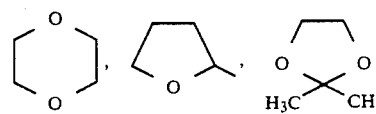

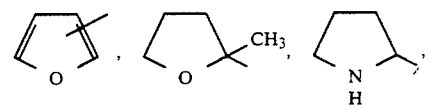

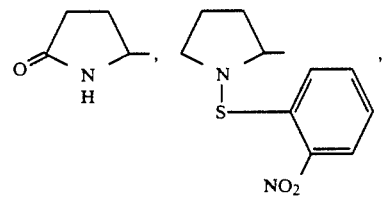

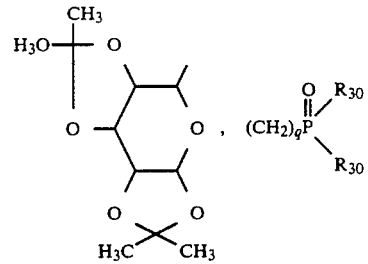

wherein $R_{30}$ is loweralkyl and q is 1, 2 or 3, and a group of the formula $R_{10}OCR_{31}R_{32}(CH_2)_n$ wherein $R_{10}$ is hydrogen or loweralkyl, $R_{31}$ is hydrogen or loweralkyl, $R_{32}$ is hydrogen or loweralkyl and n is 0, 1, 2 or 3; and (e) $R_1$ and $R_9$ taken together form a group of the formula $CHNR_{19}R_{20}$ wherein $R_{19}$ and $R_{20}$ are as hereinbeforedefined.

The present invention also relates to compounds of the formula 19

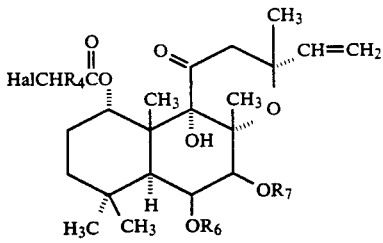

19 wherein $R_4$ is hydrogen, loweralkyl or benzyl; $R_6$ is hydrogen or a group of the formula $R_5CO$ wherein $R_5$ is hydrogen or loweralkyl; $R_7$ is hydrogen or a group of the formula $R_8CO$ wherein $R_8$ is as hereinbeforedescribed; Hal is chloro or bromo; or the optical and geometric isomers thereof, which are useful as intermediates for the preparation of the aminoacyllabdanes of the present invention.

A compound of formula 19 wherein Hal is bromo is prefered.

As used through the specification and appended claims, the term "alkyl" refers to a straight or branched chain hydrocarbon radical containing no unsaturation and having 1 to 8 carbon atoms such as methyl, ethyl, 1-propyl, 2-propyl, 1-butyl, 1-pentyl, 2-pentyl, 3-hexyl, 4-heptyl, 2-octyl, and the like; the term "alkanol" refers to a compound formed by a combination of an alkyl group and a hydroxy radical. Examples of alkanols are methanol, ethanol, 1- and 2-propanol, 1,2-dimethylethanol, hexanol, octanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, and the like; the term "halogen" refers to a member of the family consisting of fluorine, chlorine, bromine or iodine The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, and the like. The term "acyl" encompasses the term "alkanoyl" and refers to the radical derived from an organic acid by removal of the hydroxyl function. Examples of acyl radicals are tetrahydrofuroyl, 2-methyltetrahydrofuroyl, 2,2-dimethyl-1,3-dioxolanoyl, 2,3-dihydroxypropionoyl, pyroglutamoyl, N-(2-nitrophenylsulfenyl)prolyl, prolyl, methoxyacetoxy, 1,2:3,4-diisopropylidine-D-galacturonoyl, and 3-(dimethylphosphinyl)propionoyl, and the like. The term "lower" as applied to any of the aforementioned groups refers to a group having a carbon skeleton containing up to and including 6 carbon atoms.

In the formulas presented herein the various substituents are illustrated as joined to the labdane nucleus by one of two notations: a solid line (—) indicating a substituent which is in the β-orientation (i.e., above the plane of the molecule) and a broken line (- - -) indicating a substituent which is in the α-orientation (i.e., below the plane of the molecule). The formulas have all been drawn to show the compounds in their absolute stereochemical configuration. Inasmuch as the starting materials having a labdane nucleus are naturally occurring or are derived from naturally occurring materials, they, as well as the final products, have a labdane nucleus existing in the single absolute configuration depicted herein. The processes of the present invention, however, are intended to apply as well to the synthesis of labdanes of the racemic series.

In addition to the optical centers of the labdane nucleus, the substituents thereon may also contain chiral centers contributing to the optical properties of the compounds of the present invention and providing a means for the resolution thereof by conventional methods, for example, by the use of optically active acids. A wavy line (~) connecting a group to a chiral center indicates that the stereochemistry of the center is unknown, i.e., the group may exist in any of the possible orientations. The present invention comprehends all optical isomers and reacemic forms of the compounds of the present invention where such compounds have chiral centers in addition to those of the labdane nucleus.

The novel labdanes of the present invention are synthesized by the processes illustrated in Reaction Scheme A, B, and C.

To prepare a basic labdane 3 wherein $R_7$ is alkanoyl and $R_{19}$ and $R_{20}$ are as hereinbeforedescribed, a 1α,9α-dihydroxylabdane 2 wherein $R_7$ is alkanoyl is condensed with a formamide dialkylacetal of formula 10

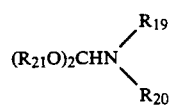

10 wherein $R_{21}$ is alkyl and $R_{19}$ and $R_{20}$ are as hereinbeforedescribed to provide a basic labdane 3. The condensation is preferably performed in the absence of an added solvent, excess formamide dialkylacetal serving both as the reactant and solvent. A dipolar aprotic solvent such as dimethylformamide, dimethylacetamide, hexamethylphosphoramide or dimethylsulfoxide may be employed, however, as the reaction medium. The temperature at which the condensation is conducted is not critical A condensation temperature within the range of about 25° to about 100° C. is generally employed to assure a reasonable rate of reaction A temperature of about 45° to about 65° C. is preferred.

To prepare a labdane of formula 4 wherein $R_{19}$ and $R_{20}$ are as before and $R_6$ is alkanoyl, a 7β-alkanoyloxy-6β-hydroxy-labdane 3 is rearranged to a 6β-alkanoyloxy-7β-hydroxylabdane 4. The rearrangement is conveniently performed in an aqueous alkanol containing an alkali metal hydroxide. Among alkanols there may be mentioned methanol, ethanol, 1- and 2-propanol and t-butanol. Methanol is preferred. Among alkali metal hydroxides there may be included lithium, sodium and potassium hydroxide. Sodium hydroxide is preferred. While the rearrangement is preferably performed at about ambient temperature, it may be conducted at a reduced temperature within the range of about 0° to about 25° C., or at an elevated temperature of about 25° to 35° C.

The rearrangement may preferably be effected, for example, by treating 3 with lithium 1,1,1,3,3,3-hexamethyldisilazide in an ethereal solvent such as tetrahydrofuran, dioxane, 1,2-dimethoxyethane or bis-(2-methoxyethyl)ether at a reduced temperature of about 0° C.

To furnish a basic labdane of formula 5 wherein $R_{19}$ and $R_{20}$ are as above, a 6β-alkanoyloxy-7β-hydroxylabdane 4 is hydrolyzed to the 6β,7β- dihydroxylabdane 5. The hydrolysis is carried out in an aqueous alkanol such as aqueous methanol, ethanol, 1- or 2-propanol or t- butanol, aqueous methanol being preferred, containing an alkali carbonate such as lithium, sodium or potassium carbonate, potassium carbonate being prefered, at a hydrolysis temperature within the range of about 10° to about 75° C., a hydrolysis temperature of about 25° C. being preferred.

A 6β,7β-dihydroxylabdane of formula 5 may also be prepared by hydrolysis of a 7β-alkanoyloxy-6β-hydroxylabdane of formula 3 by means of the hereinbeforedescribed processes for the conversion of 4 to 5.

To introduce a 6β,7β-sulfite or 6β,7β-carbonate function into the basic labdane nucleus, i.e., to prepare a compound of formula 7 wherein X is SO or CO, respectively, a 6β,7β-dihydroxylabdane of formula 5 is treated with a compound of formula 11.

HalXHal                                                         11 wherein Hal is bromo or chloro, preferably chloro, and X is SO or CO in the presence of an organic base such as trimethyl- or triethylamine, pyridine, lutidine or collidine at a reduced temperature within the range of about −25° to about 25° C. The preferred organic base is pyridine and the preferred reaction temperature is about 0° C.

To elaborate a basic labdane characterized by the presence of aminoacyloxy and aminoacetal moieties, a 7β-hydroxylabdane 5 is esterified with an aminoacid of formula 12.

$R_{11}R_{12}NCHR_{13}CO_2H$                                   12 wherein $R_{11}$, $R_{12}$ and $R_{13}$ are as hereinbeforedescribed. The esterification is conveniently effected in a halocarbon such as dichloromethane or tirchloromethane in the presence of a carbodiimide such as dicyclohexylcarbodiimide and a catalyst such as 4-(N,N-dimethylamino)-pyridine at a reaction temperature within the range of about 0° to about 50° C. Dichloromethane and dicyclohexylcarbodiimide are the preferred halocarbon and carbodiimide, respectively. A reaction temperature of about 25° C. is also preferred. A hydrohalide of the aminoacid, for example, an aminoacid hydrochloride, may be employed in the process for the esterification of a 7β-hydroxylabdane.

To construct a basic labdane characterized by an aminoacyloxy function at the 7β-position and a free hydroxy group at the 1 -position of the labdane nucleus, i.e., to synthesize a compound of formula 9 wherein $R_{11}$, $R_{12}$ and $R_{13}$ are as hereinbeforedefined, a 7β-alkanoyloxylabdane 2 is hydrolyzed under conventional conditions utilizing an alkali metal carbonate such as sodium carbonate in an aqueous alkanol such as methanol at a reaction temperature of about 25° C. to the known 1α,6β,7β,9α-tetrahydroxy labdane 8 which is esterified with a compound of the formula 12.

$R_{11}R_{12}NCHR_{13}CO_2H$                                   12 wherein $R_{11}$, $R_{12}$ and $R_{13}$ are as hereinbeforedefined under reaction conditions substantially similar to those employed for the conversion of 5 to 6 described above.

Alternatively, basic labdanes of formula 9 may be prepared by hydrolysis of the aminoacetal moiety of labdanes of formula 6. The hydrolysis may be accomplished by treating an aminoacetal of formula 6 with an alkanoic acid such as acetic or propanoic acid, preferably acetic acid, in an aqueous alkanol such as methanol, ethanol or 1- or 2-propanol, preferably aqueous methanol, at a temperature within the range of about 0° to 50° C., preferably at a temperature of about 25° C.

Basic labdanes of formula 9 are also prepared by desilylation of a compound of formula 15. The removal of the silyl group is achieved by, for example, treating the 1α-silyoxylabdane 5 with aqueous hydrogen fluoride in acetonitrile at a temperature of about 25° C.

To gain entry into the labdane system having a basic moiety at the 7β-position and a silyloxy group at the 1α-position, i.e., to provide basic labdanes of formula 15 wherein $R_3$, $R_4$, $R_5$, $R_{11}$, $R_{12}$, and $R_{13}$ are as above, a 7β-alkanoyloxy-1α-hydroxylabdane 2 is silylated to a 7β-alkanoyloxy-1α-silyloxylabdane 13 which is hydrolyzed to a 7β-hydroxy-1α-silyloxylabdane 14 and converted to a basic labdane 15.

To effect the silylation, one treats a 1α-hydroxylabdane 2 with a N-(trialkylsilyl)-N-alkyltrifluoroacetamide of formula 16

$R_3R_4R_5SiNR_{23}COCCF_3$                                   16 wherein $R_3$, $R_4$ and $R_5$ are as above and $R_{23}$ is alkyl, preferably a trifluoroacetamide wherein $R_{23}$ is alkyl, most preferably N-(t-butyldimethylsilyl)-N-methyltrifluoroacetamide, in a dipolar aprotic solvent such as dimethylformamide, dimethylacetamide, hexamethylphosphoramide or dimethylsulfoxide, preferably dimethylformamide, at a temperature within the range of about 0° to 75° C., preferably at a reaction temperature of about 25° C., to afford a compound of formula 13.

The hydrolysis is accomplished by treating a 7β-alkanoyloxy-1α-trialkylsilyloxylabdane 13 with an alkali metal carbonate in an aqueous alkanol. Included among alkali metal carbonates are lithium, sodium and potassium carbonate. Included among alkanols are methanol, ethanol, 1- and 2- propanol and t-butanol. Potassium carbonate and methanol are the preferred alkali metal carbonate and alkanol. While the reaction temperature is not narrowly critical, it is preferable to perform the hydrolysis at an elevated temperature within the range of about 60° to about 100° C. A hydrolysis temperature of about 80° C. is most preferred.

The introduction of the basic moiety at the 7β-position of the labdane nucleus, i.e., the conversion of a 7β-hydroxylabdane 14 to a 7β-aminoalkylcarbonyloxylabdane 15 is acnieved by processes substantially similar to those employed for the conversion of 7 -hydroxylabdane 5 to 7β-aminoalkylcarbonyloxylabdane 6. For example, one treats a 7α-hydroxylabdane 14 with an aminoacid 12, free or as the hydrohalide salt, in a halocarbon solvent such as dichloromethane in the presence of a catalyst such as 4-dimethylaminopyridine and a carbodiimide such as dicyclohexylcarbodiimide at about ambient temperature (ca. 25° C.) to provide a compound of formula 15.

To synthesize a labdane having a 6β,7β-sulfite or 6β,7β-carbonate function and a 1α-hydroxy group, i.e., a compound of formula 18 wherein X is SO or CO, a 1α-silyloxylabdane of formula 14 is converted to a 1α-silyloxylabdane -6β,7β-sulfite or -carbonate of formula 17 by processes substantially similar to those employed for the conversion of a compound of formula 5 to a compound of formula 7 followed by desilylation by the process described above for the transformation of a 1α-silyloxylabdane 15 to a 1α-hydroxylabdane 9.

To prepare an aminoacyllabdane 2 wherein $R_6$ or $R_7$ is acyl, a 1α-hydroxylabdane 2 wherein $R_6$ or $R_7$ is acyl is acylated with a haloalkylcarbonyl halide of the formula 19

$$HalCHR_{26}COHal \qquad 19$$

wherein $R_{26}$ is as hereinbeforedescribed and Hal is chloro or bromo to provide a 1α-haloalkanoyloxylabdane 20 which is condensed with an amine of the formula 21

$$R_2R_3NH \qquad 21$$

to afford 22.

The acylation of hydroxylabdane 2 is readily accomplished by treating a hydroxylabdane 2 with a haloalkylcarbonyl halide 19 such as bromoalkylcarbonyl bromide or a chloroalkylcarbonyl chloride, a bromoalkylcarbonyl bromide being preferred, in a halocarbon in the presence of a tertiary amine. Among halocarbons, there may be mentioned dichloromethane, trichloromethane, 1, 1- and 1,2-dichloromethane and 1,1- and 1,2-dichloroethene. Dichloromethane is the preferred halocarbon. Among tertiary amines, there may be mentioned, for example, 4-dimethylaminopyridine and N,N-dimethylaniline. N,N-Dimethylaniline is the preferred amine. While the temperature at which the acylation is performed is not narrowly critical, it is preferred to conduct the reaction at a temperature within the range of about −0° to about 50° C. It is most preferred to perform the acylation at a temperature within the range of about 0° to about 25° C.

The condensation is effected by treating a haloalkanoyloxylabdane 20 with a primary or secondary amine 21 in an alkyl alkanoate or halocarbon, or a mixture thereof. Included among alkyl alkanoates are methyl acetate, ethyl acetate and ethyl propanoate. Included among halocarbons are dichloromethane, trichloromethane, 1,1- and 1,2-dichloromethane. Ethyl acetate and dichloromethane are the preferred solvents. The condensation is preferably performed in the absence of added base. An alkali metal bicarbonate such as lithium, sodium or potassium bicarbonate may, however, be utilized The condensation temperature is not critical. The converstion proceeds readily at a temperature within the range of about 0° to about 50° C. A reaction temperature of about 25° C. is preferred.

To introduce a 7β-acyloxy function into the labdane nucleus, i.e., to prepare a compound of formula 25 wherein $R_7$ is acyl, a 7β-hydroxylabdane of formula 23 is treated with an organic acid of the formula $$R_8CO_2H \qquad 24$$

wherein $R_8$ is as hereinbeforedescribed in a halocarbon such as dichloromethane or trichloromethane in the presence of a carbodiimide such as dicyclohexylcarbodiimide or 1-(3-dimethylaminopropyl)-3-ethylcarbodiimide and a catalyst such as 4-(N,N-dimethylamino)pyridine or 4-(N-pyrrolidyl)pyridine at a reaction temperature within the range of about 0° to about 50° C. Dichloromethane is the preferred solvent. A reaction temperature of about 25° C. is also preferred.

To prepare a 6β-acyloxylabdane 26 wherein $R_6$ is acyl, a 7β-acyloxylabdane 25 is rearranged to 26 by means of an alkali metal bis(triloweralkylsilyl)amide in an ethereal or hydrocarbon solvent at a reduced temperature of about −25° C. to about 25° C., a temperature of about 0°C. being preferred. Suitable ethereal solvents include tetrahydrofuran, dioxane, 1,2-dimethoxyethane and bis(2-methoxyethyl)ether. Tetrahydrofurane is preferred. Suitable alkali metal bis(triloweralkylsilyl)amides include lithium, sodium and potassium bis(trimethyl-, triethyl- and tripropylsilyl)amide. Lithium bis(trimethylsilyl)amide is preferred.

To prepare an acyloxylabdane of formula 25 or 26 characterized by the presence of a dihydroxyalkanoyl group at the 7β- or 6β-position, respectively, a dioxolanoyloxylabdane of formula 25 or 26 wherein $R_7$ or $R_8$ is dioxolanoyl is cleaved to afford the desired dihydroxyalkanoyl derivative. The cleavage is accomplished by contacting the dioxolanoyllabdane 25 or 26 with an alkanoic acid or an aqueous alkanoic acid is an alkanol. Among alkanoic and aqueous alkanoic acids, there may be mentioned acetic acid, aqueous acetic acid, proprionic acid, aqueous propionic acid and the like. Among alkanols there may be mentioned methanol, ethanol, 1- and 2-propanol, t-butanol and the like. Aqueous acetic acid is preferred. Acetic acid (80%) is most preferred. Methanol is also preferred. While the cleavage proceeds readily at a reaction temperature within the range of about 0° to aobut 65° C., a reaction temperature within the range of about 25° to 50° C. is preferred.

The labdane starting materials for the processes of the present invention, i.e., labdanes of formula 3 wherein $R_7$ is hydrogen or a group of the formula $R_8CO$ wherein $R_8$ is as hereinbeforedescribed, are described in U.S. Pat. No. 4,134,986, issued Jan. 16, 1979 to B. S. Bajwa, et al., or may be prepared from compounds disclosed therein by conventional processes.

The labdanes of the present invention are useful in the treatment of elevated intraocular pressure by virtue of their ability to reduce intraocular pressure as determined by the method described by J. Caprioli, et al., Invest. Ophthalmol. Vis. Sci., 25, 268 (1984). The results of the determination expressed as percent decrease of outflow pressure is presented in the Table.

TABLE

| COMPOUND | CONCENTRATION (%) | DECREASE IN OUTFLOW PRESSURE (%) |
|---|---|---|
| 7β-(N,N-diethylaminoacetoxy)-8,13-epoxy-1α,6β,9α-trihydroxylabd-14-en-11-one 1,9-dimethylformamide acetal | 2 | 36 |
| 7β-(N-acetylaminoacetoxy)-8,13-epoxy-1α,6β,9α,trihydroxylabd-14-en-11-one | 2 | 59 |
| 7β-[2-[(N-t-butoxycarbonyl)amino]propanoyloxy]-8,13-epoxy-1α,6β,9α-trihydroxylabd-14-en-11-one | 1 | 43 |
| 7β-(N,N-diethylaminoacetoxy)-8,13-epoxy-1α,6β,9α-trihydroxylabd-14-en-11-one | 2 | 27 |
| 7β-(N,N-dimethylaminoacetoxy)-8,13-1α,6β,9α-trihydroxylabd-14-en-11-one | 2 | 30 |
| 8,13-epoxy-1α,6β,9α-trihydroxy-7β-(2-tetrahydrofuranoyloxy)labd-14-en-11-one | 2 | 51 |
| 7β-acetoxy-8,13-epoxy-1α,6β,9α-trihydroxy- | 1.0 0.1 | 51 23 |

TABLE-continued

| COMPOUND | CONCENTRATION (%) | DECREASE IN OUTFLOW PRESSURE (%) |
| --- | --- | --- |
| labd-14-en-11-one | | |

Intraocular pressure reduction is achieved when the present labdanes are administered to a subject requiring such treatment as an effective topical dose of a 0.01 to 3.0% solution or suspension. A particularly effective amount is about 3 drops of a 1% preparation per day. It is to be understood, however, that for any particular subject, specific dosage regimens should be adjusting according to the individual need and the professional judgment of the person administering or supervising the administration of the aforesaid compound. It is to be further understood that the dosages set forth herein are exemplary only and that they do not, to any extent, limit the scope or practice of the invention.

Compounds of the present invention are also useful for the treatment of hypertension, congestive heart failure, bronchial asthma and psoriasis.

Compounds of the present invention include:

(1) 1α-acetoxy-7β-(N,N-dimethylaminoacetoxy)-8,13-epoxy-6β,9α-dihydroxylabd-14-en-11-one.

(2) 7β-(N,N-dimethylaminoacetoxy)-8,13-epoxy-6β-hydroxylabd-14-en-11-one 1α,9α-sulfite.

(3) 7β-(N,N-dimethylaminoacetoxy)-8,13-epoxy-1α,6β,9α-trihydroxylabd-14-en-11-one 1,9-pyrrolidineformamide acetal.

(4) 6β-[N-(t-butoxycarbonyl)aminoacetoxy]-8,13-epoxy-1α,7β, 9α-trihydroxylabd-14-en-11-one.

(5) 8,13-epoxy-7β-formyloxy-b 1α,6β,9α-trihydroxylabd-14-en-11-one 1,9 dimethylformamide acetal.

(6) 7β-(N,N-dimethylaminoacetoxy)-8,13-epoxy-1α-formloxy 6β,9α-dihydroxylabd-14-en-11-one.

(7) 7β-(N,N-dimethylaminoacetoxy)-8,13-epoxy-6β-hydroxylabd-14-en-11-one 1α,9α-carbonate.

(8) 7β-(N,N-dimethylaminoacetoxy)-8,13-epoxy-1α,6β,9α-trihydroxylabd-14-en-11-one 1,9 piperidineformamide acetal.

(9) 7β-(N,N-dimethylaminoacetoxy)-8,13-epoxy-1α,6β,9α-trihydroxylabd-14-en-11-one 1,9 morpholineformamide acetal.

(10) 7β-(N,N-dimethylaminoacetoxy)-8,13-epoxy-1α,6β,9α-trihydroxylabd-14-en-11-one 1,9 thiomopholineformamide acetal.

(11) 8,13-epoxy-1α,9α-dihydroxylabd-14-en-one 1,9-dimethylformamide acetal 6β,7β-carbonate.

(12) 7β-aminoacetoxy-8,13-epoxy-1α,6β,9α-trihydroxylabd-14-en-11-one.

(13) 7β-(1-piperidinoacetoxy)-8,13-epoxy-1α,6β,9α-trihydroxylabd-14-en-11-one.

(14) 7β-(1-pyrrolidinoacetoxy)-8,13-epoxy-1α,6β,9α-trihydroxylabd-14-en-11-one.

(15) 7β-(4-morpholinoacetoxy)-8,13-epoxy- 1α,6β,9α-trihydroxylabd-14-en-11-one.

(16) 7-β(4-thiomopholinoacetoxy)-8,13-epoxy-1α,6β,9α-trihydroxylabd-14-en-11-one.

(17) 8,13-epoxy-1α,6β,9α-trihydroxy-7β-(2-aminopropionyloxy)labd-14-en-11-one.

(18) 8,13-epoxy- 1α,6β, 9α-trihydroxy-7β-(2-amino-3-phenylpropionyloxy)labd-14-en-11-one.

(19) 7β-(2,3-dihydroxy-2-methylpropionyloxy)-8,13-epoxy-1α,6β,9α-trihydroxylabd-14-en-11-one.

(20) 8,13-epoxy-7β-(3-hydroxy-2,2-dimethylpropionyloxy)-1α,6β,9α-trihydroxylabd-14-en-11-one.

(21) 8,13-epoxy-7β-(2-hydroxymethyl-2-hydroxybutyroyloxy)-1α,6β,9α-trihydroxylabd-14-en-11-one.

(22) 8,13-epoxy-7β-(2,2-dihydroxymethylpropionyloxy)-1α,6β,9α-trihydroxylabd-14-en-11-one.

(23) 8,13-epoxy-7β-(2,2-dihydroxymethyl-3-hydroxypropionyloxy)-1α,6β,9α-trihydroxylabd-14-en-11-one.

Effective amounts of the compounds of the present invention may be administered to a subject by any one of various methods, for example, orally as in capsules or tablets, parenterally in the form of sterile solutions or suspensions, in some cases intravenously in the form of sterile solutions, or suspensions, and topically in the form of solutions, suspension or ointments, and by aerosol spray. The labdanes of the present invention, while effective themselves, may be formulated and administered in the form of their pharmaceutically acceptable addition salts for purposes of increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, citric acid and the like.

Effective quantities of the compounds of the invention may be administered orally, for example, with an inert diluent or with an edible carrier They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 0.1-30 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral or topical therapeutic administeration, the active compounds of the invention may be incorporated into a solution, suspension, ointment or cream. These preparations should contain at least 0.01% of active compound, but may be varied between 0.5 and about 5% of the weight thereof. The amount of active compounds in such compositions is such that a suitable dosage will be obtained. Preferred compositions and preparations according to the present invention are prepared so that a parenteral dosage unit contains between 0.01 to 10 milligrams of active compound.

The solutions or suspensions for topical or parenteral administration may also include the following components: a sterile diluent such as water for injection, saline solution, fixed oils, polyethylene glycols, glycerine, proplyene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules or disposable syringes; the topical preparation may be enclosed in multiple dose vials or dropping bottles, made of glass or plastic.

The following examples are for illustrative purposes only and are not to be construed as limiting the invention. All temperatures are given in degrees Centigrade.

EXAMPLE 1

7$\beta$-Acetoxy-8,13-epoxy-1$\alpha$,6$\beta$,9$\alpha$-trihydroxylabd-14-en-11-one-1,9-dimethylformamide acetal 7$\beta$-Acetoxy-8,13-epoxy-1$\alpha$,6$\beta$,9$\alpha$-trihydroxylabd-14-en-11-one 100 mg) was dissolved in 1 ml of dimethylformamide dimethyl-acetal. The mixture was stirred 1 hr at room temperature and overnight at 55° under nitrogen. The mixture was dissolved in ether, washed with water, dried over anhydrous sodium sulfate, filtered and concentrated to an oil. The oil was dissolved in a minimum volume of dichloromethane and chromatographed using 10 g of silica gel (230–400 mesh). Eluent: 8×3 ml of dichloromethane, 8×3 ml of 3% methanol/dichloromethane and 8×3 ml of 5% methanol/dichloromethane. Evaporation of the solvent from appropriate fractions followed by drying at 60° (1 mm) provided 90 mg (79 1%) of product as an oil.

ANALYSIS: Calculated for $C_{25}H_{39}NO_7$:64.49% C, 8.44% H, 3.01% N, Found: 64.69% C, 8.25% H, 3.09% N.

EXAMPLE 2

6$\beta$-Acetoxy-8,13-epoxy-1$\alpha$,7$\beta$,9$\alpha$-trihydroxylabd-14-en-11-one-1,9-dimethylformamide acetal A solution of 200 mg of 7$\beta$-acetoxy-8,13-epoxy-1$\alpha$,6$\beta$,9$\alpha$-trihydroxylabd-14-en-11-one in 2 ml of dimethylformamide dimethylacetal was stirred at 35° overnight, under nitrogen, and allowed to cool to room temperature. To the mixture was added 10 ml of an 20% aqueous methanolic solution of sodium hydroxide. The mixture was stirred overnight at room temperature. The mixture was diluted with ethyl acetate, washed twice with water, saturated sodium chloride solution and dried over anhydrous sodium sulfate. Filtration followed by evaportion of solvent provided an oil. The material was flash chromatographed using 20 g of silica gel (230–400 mesh) (eluent: 50×15 ml of 30/70 ethyl acetate/hexane). Evaporation of the appropriate fractions followed by drying at 80° (1 mm) provided 81 mg (35.6%) of product, mp 173°–175°.

ANALYSIS: Calculated for $C_{25}H_{39}NO_7$: 64.49% ,C 8.44% H, 3.01% N, Found: 64.59% C, 8.56% H, 2.86% N.

EXAMPLE 3

8,13-Epoxy-1$\alpha$,6$\beta$,7$\beta$,9$\alpha$-trihydroxylabd-14-en-11-one-1,9-dimethylformamide acetal A solution of 225 mg of 7$\beta$-acetoxy-8.13-epoxy-1$\alpha$,6$\beta$,9$\alpha$-tetrahydroxylabd-14-en-11-one-1,9-dimethylformamide acetal was stirred at room temperature under nitrogen for 5 hrs in 5 ml of saturated potassium carbonate solution in 20% aqueous methanol. The solution was diluted with water and extracted twice with ether. The ether extracts were washed twice with water and dried over anhydrous sodium sulfate. Filtration followed by evaporation of the solvent provided an oil, which crystallized on standing. The crystals were dried at 113° (1 mm) to yield 192 mg (88.5%) of product, mp 136°–144°.

ANALYSIS: Calculated for $C_{23}H_{37}NO_6$: 65.22% C, 8.81% H, 3.31% N, Found: 65.18% C, 8.76% H, 3.25% N.

EXAMPLE 4

8,13-Epoxy-1$\alpha$,9$\alpha$-dihydroxylabd-14-en-11-one-1$\alpha$,9$\alpha$-dimethyformamide acetal -6$\beta$,7$\beta$-sulfite To a stirred solution of 200 mg of 8,13-epoxy-1$\alpha$,6$\beta$,7$\beta$,9$\alpha$-tetrahydroxylabd-14-en-11-one-1$\alpha$,9$\alpha$-dimethylformamide acetal in 2 ml of dry pyridine was added slowly, dropwise, a solution of 0.2 ml of thionyl chloride in 4 ml of dry pyridine. The mixture was stirred 15 min at 0°, poured into water, and extracted twice with ether. The extracts were washed twice with water, dried over anhydrous sodium sulfate and filtered. Concentration provided an oil. The material was dissolved in a minimum volume of 25% ethyl acetate/hexane and purified by flask chromatography on 25 g of silica gel (230–400 mesh; eluent: 20×15 ml of 25% ethyl acetate/hexane). Concentration of the appropriate fractions followed by drying at 40° (1 mm) provided 0.148 g (66.7%) of product, mp 157°–162°.

ANALYSIS: Calculated for $C_{23}H_{35}NO_7S$: 58 82% C, 7.51% H, 2.98% N, Found: 58.72% C, 7.51% H, 2.56% N.

EXAMPLE 5

7$\beta$-[N-(t-Butoxycarbonyl)aminoacetoxy]-8,13-epoxy-1$\alpha$,6$\beta$,9$\alpha$-trihydroxylabd-14-en-11-one To a mixture of 100 mg of 8,13-epoxy-1$\alpha$,6$\beta$,7$\beta$,9$\alpha$-tetrahydroxylabd-14-en-11-one, 34.1 mg of 4-dimethylaminopyridine and 47.6 mg of N-t-butoxycarbonylglycine dissolved in 5 ml of dichloromethane was added a solution of 61.6 mg of dicyclohexylcarbodiimide dissolved in 2 ml of dichloromethane. The mixture was stirred under nitrogen for 4 hr. The mixture was filtered and the filtrate was evaporated to dryness. The residue was purified by flash chromatography on silica gel in hexane:ethyl acetate (3:1). The appropriate fractions were combined and evaporated to dryness under vacuum. The residue was crystallized from hexane, filtered and dried yielding 107.3 mg (75.2%) of product, mp 94°–100°.

ANALYSIS: Calculated for $C_{27}H_{43}NO_9$: 61.68% C, 8.26% H, 2.66% N, Found: 62.12% C, 8.58% H, 2.57% N.

EXAMPLE 6

7β-(N,N-Diethylaminoacetoxy)-8,13-epoxy-1α,6β,9α-trihydroxylabd-14-en-11-one-1α,9α-dimethylformamide acetal To a mixture of 150 mg of 8,13-epoxy-1α,6β,7β,9α-tetrahydroxylabd-14-en-11-one dimethylformamide acetal, 59.4 mg of diethylglycine hydrochloride, 44.6 mg of 4-(N,N-dimethylamino)pyridine in 6 ml of dichloromethane was added 80.5 mg of dicyclohexylcarbodiimide dissolved in 3 ml of dichloromethane. The mixture was stirred under nitrogen at ambient temperature overnight. The mixture was filtered and evaporated to dryness under vacuum. The residue was flash chromatographed in hexane:ethyl acetate (1:1). The appropriate fractions were combined and evaporated to dryness to yield 138.3 mg (72.8%) of product, mp 129°–133°.

ANALYSIS: Calculated for $C_{29}H_{48}N_2O_7$: 64.89% C, 9.03% H, 5.22% N, Found: 65.17% C, 8.87% H, 5.46% N.

EXAMPLE 7

7β-Acetoxy-1α-(t-butyldimethylsilyloxy)-6β,9α-dihydroxy-8,13-epoxylabd-14-en-11-one To a solution of 1.00 g of 7β-aceotxy-8,13,epoxy-1α,6β,9α-tribydroxylabd-14-en-11-one in 5 ml of dimethylformamide was added, dropwise, 610 ul of N-(t-butyldimethylsilyl)-N-methyltrifluoroacetamide, and the reaction mixture was stirred for 1 hr. The mixture was allowed to stand at room temperature overnight, and was then diluted with 5 ml of one-half saturated brine and extracted with diethyl ether. The combined extracts were dried over anhydrous sodium sulfate, filtered and the filtrates were evaporated. The residue was flash chromatographed on a silica gel column using ethyl acetate-hexane (1:3) as the eluent. Evaporation of the appropriate fractions gave 1.24 g (97.2%) of product.

EXAMPLE 8

1α-(t-Butyldimethylsilyloxy)-8,13-epoxy-6β,7β,9α-trihydroxylabd-14-en-11-one

A solution of 1.24 g of 7β-acetoxy-1α-(t-butyldimethylsilyloxy)-8,13-epoxy-6β,9α-dihydroxylabd-14-en-11-one, 4 ml of saturated potassium carbonate solution and 16 ml of methanol was heated at 80° for 1 hr. The reaction mixture was cooled, diluted with saturated sodium chloride solution, and extracted with ether. The combined ether extracts were dried over anhydrous potassium carbonate, filtered, and the filtrate was evaporated. The residue was flash chromatographed on silica gel column using ethyl acetate-hexane (1:3) as the eluent. Evaporation of the appropriate fractions provided 646 mg (56.5%) of product.

EXAMPLE 9

7β-(N,N-Dimethylaminocetoxy)-8,13-epoxy-6β,9α-dihydroxy-1α-(t-butyldimethylsilyloxy) labd-14-en-11-one hydrochloride 8,13-Epoxy-6β,7β,9α-trihydroxy-1α-(t-butyldimethylsilyloxy)labd-14-en-11-one (100 mg) was dissolved in 4 ml of dichloromethane with 29.0 mg of dimethylglycine hydrochloride and 26 0 mg of 4-dimethylaminopyridine. To the above mixture was added 48 mg of N,N-dicyclohexylcarbodiimide dissolved in 1 ml of dichloromethane. The mixture was stirred at ambient temperature for 18 hr. The mixture was filtered through a cotton plug and the filtrate was evaporated to dryness. The residue was suspended in ether, filtered and evaporated to dryness. The residue was flash chromatographed on silica gel in hexane:ethyl acetate methanol (10:10:1). The appropriate fractions were combined and evaporated to dryness to provide 87.8 mg (74.7%) of product. The product was dissolved in ether and the hydrochloride precipitated, mp 227°–228°.

ANALYSIS: Calculated for $C_{30}H_{54}ClNO_7Si$: 59.61% C, 9.02% H, 2.32% N, Found: 60.06% C, 9.22% H, 2.19% N.

EXAMPLE 10

7β-(N,N-Diethylaminoacetoxy)-8,13-epoxy-6β,9α-dihydroxy-1α-(t-butyldimethylsilyloxy)labd-14-en-11-one hydrochloride 8,13-Epoxy-6β,7β,9α-trihydroxy-1α-(t-butyldimethylsilyloxy)labd-14-en-11-one (50 mg) was combined with 17.4 mg of N,N-diethylglycine hydrochloride and 13.1 mg of 4-(N,N-dimethyl amino)pyridine in 2 ml of dry dichloromethane. Dicylohexylcarbodiimide (24 mg) dissolved in 1 ml of dichloromethane was added to the above mixture in a sealed tube. The mixture was allowed to stand at ambient temperature overnight. The dicyclohexylurea was filtered off. After the filtrate was evaporated to dryness, the residue was suspended in ethyl acetate and filtered. The filtrate was flash chromatographed on silica gel in hexane:ethyl acetate (3:1). The appropriate fractions were combined and evaporated to dryness under vacuum. The residue was dissolved in ether, from which the product as the hydrochloride was precipitated, and yielded 32.7 mg of product, mp 200°–210°.

ANALYSIS: Calculated for $C_{32}H_{58}ClNO_7Si$: 60.77% C, 9.26% H, 2.21% N, Found: 60.88% C, 9.68% H, 2.33% N.

EXAMPLE 11

7β-(N,N-Dimethylaminoacetoxy)-8,13-epoxy-1α,6β,-9α-trihydroxylabd-14-en-11-one hydrochloride 7β-(N,N-Dimethylaminoacetoxy)-8,13-epoxy-1α,6β,9α-trihydroxylabd-14-en-11-one dimethylformamide acetal (103.1 mg) was dissolved in a mixture of 1.4 ml of methanol and 1.4 ml of 80% acetic acid. The mixture was stirred at ambient temperature for 3 days after which it was evaporated to dryness. The residue was dissolved in ether and extracted several times with 5% sodium bicarbonate solution. The organic phase was dried over anhydrous sodium sulfate, filtered and evaporated to dryness. The residue was flash chromatographed on silica gel packed in hexane:ethyl acetate:methanol (10:10:1). The appropriate fractions evaporated to dryness. The residue was dissolved in ether and treated with ethereal hydrogen chloride to afford 28 mg (30.5%) of product, mp 255°–260° (dec).

ANALYSIS: Calculated for $C_{24}H_{40}ClNO_7$: 58.81% C, 8.24% H, 2.86% N, Found: 58.77% C, 8.19% H, 2.73% N.

EXAMPLE 12

7β-(N,N-Diethylaminoacetoxy)-8,13-epoxy-1α,6β,9α-trihydroxylabd-14-en-11-one hydrochloride 7β-(N,N-diethylaminoacetoxy)-8,13-epoxy-1α,6β, 9β-trihydroxylabd-14-en-11-one 1,9-dimethylformamide acetal (84.1 mg) was dissolved in 2 ml of a mixture of methanol:acetic acid:water (10:8:2) and allowed to stand overnight under nitrogen at ambient temperature. The mixture was basified with saturated aqueous sodium bicarbonate solution. The product was extracted into dichloromethane, dried over anhydrous sodium sulfate, filtered and evaporated. The residue was dissolved in ether and treated with ethereal hydrogen chloride. The ether suspension was evaporated and the residue was resuspended in ether. The solid was filtered and dried under vacuum at 80° for 1 hr to yield 42.2 mg (52.0%) of product, mp 149°-156° (dec).

ANALYSIS: Calculated for $C_{26}H_{43}ClNO_7$: 60.26% C, 8.58% H, 2.70% N, Found: 59.66% C, 8.52% H, 3.11% N.

EXAMPLE 13

7β-(Methoxyacetoxy)-8,13-epoxy-1α,6β,9α-trihydroxylabd-14-en-11-one 8,13-Epoxy-1α,6β,7β,9α-tetrahydroxylabd-14-en-11-one (100 mg) was dissolved in 5 ml of dichloromethane together with 34.2 mg of 4-dimethylaminopyridine and 24.5 mg of methoxyacetic acid. To the above solution was added 61.7 mg of dicyclohexylcarbodiimide dissolved in 2 ml of dichloromethane, and the mixture was stirred overnight under an atmosphere of nitrogen. The mixture was filtered, evaporated to dryness and loaded onto a flash silica gel column packed in dichloromethane:methanol (10:0.2). The appropriate fractions were combined and evaporated to dryness. Trituration of the residue with hexane provided 49.5 mg (41.4%) of product, mp 164°-170°.

ANALYSIS: Caculated for $C_{23}H_{36}O_8$: 70% C, 8 25% H, Found: 62.51% C, 8.22% H.

EXAMPLE 14

7β-[2-(N-t-Butoxycarbonyl)aminopropanolyoxy]-8,13-epoxy-1α,6β, 9α-trihydroxylabd-14-en-11-one 8,13-Epoxy-1α,6β,7β,9α-tetrahydroxylabd-14-en-11-one (100 mg) was stirred with 34.2 mg of 4-dimethylaminopyridine and 51.4 mg of N-t-butoxycarbonyl-L-alanine in 5 ml of dichloromethane. Dicyclohexylcarbodiimide (61.7 mg) dissolved in 2 ml of dichloromethane was added to the mixture and was allowed to stand overnight under nitrogen at ambient temperature. The mixture was diluted with ether, filtered and evaporated to dryness. The residue was flash chromatographed on silica gel packed in hexane:ethyl acetate (3:1). The appropriate fractions were combined and evaporated to dryness. Trituration of the residue with hexane provided 74.1 mg (50.6%) of product, mp 117°-122° (dec).

ANALYSIS: Calculated for $C_{28}H_{45}NO_9$: 62.31% C, 8.42% H, 2.59% N, Found: 62.20% C, 8.39% H, 2.99% N.

EXAMPLE 15

7β-(N-Acetylaminoacetoxy)-8,13-epoxy-1α,6β,9α-trihydroxylabd-14-en-11-one 8,13-Epoxy-1α,6β,7β,9α-tetrahydroxylabd-14-en-11-one (100 mg) was stirred with 34.2 mg of 4-dimethylaminopyridine and 31.8 mg of N-acetylglycine in 5 ml of dichloromethane. Dicyclohexylcarbodiimide (61.7 mg) dissolved in 2 ml of dichloromethane was added to the solution and the resultant mixture was stirred under nitrogen at ambient temperature overnight. The mixture was filtered and evaporated to dryness. The residue was flash chromatographed on silica gel packed in hexane:ethyl acetate (1:1). The appropriate fractions were combined and evaporated to dryness. The residue was triturated with cyclohexane affording 26.6 mg (21.0%) of product, mp 106°-110°.

ANALYSIS: Calculated for $C_{24}H_{37}NO_8$: 61.64% C, 7.99% H,. 2.99% N, Found: 62.01% C, 8.27% H, 2.60% N.

EXAMPLE 16

7β-(4-Morpholinoacetoxy)-8,13-epoxy-1α,6β,9α-trihydroxylabd-14-en-11-one hydrochloride hydrate 8,13-Epoxy-1α,6β,7β,9α-tetrahydroxylabd-14-en-11-one (100 mg) was dissolved in 5 ml of dichloromethane and stirred with 34.2 mg of 4-N,N-dimethylaminopyridine and 49.3 mg of (4-morpholino)acetic acid hydrochloride. Dicyclohexyl carbodiimide (61.7 mg) in 2 ml of dichloromethane was added to the mixture and was stirred under nitrogen overnight at ambient temperature. The mixture was diluted with ether and filtered. The filtrate was evaporated. The residue was flash chromatographed on silica gel in hexane:ethyl acetate (1:1) and eluted with hexane:ethyl acetate:methanol (10:10:1). The appropriate fractions were combined and evaporated. The residue was dissolved in ether and treated with ethereal hydrogen chloride to yield 55.5 mg (38.4%) of product, mp 165°-175° (dec).

ANALYSIS: Calculated for $C_{26}H_{44}ClNO_9$: 56.76% C, 8.08% H, 2.54% N, Found: 57.01% C, 7.69% H, 2.77% N.

EXAMPLE 17

7β-[N-(2-Nitrophenylsulfenyl)aminoacetoxy]-8,13-epoxy-1α,6β,9α-trihydroxylabd-14-en-11-one 8,13-Epoxy-1,60 ,6β,7β,9α-trihydroxylabd-14-en-11-one (325 mg), 361.7 mg of N-(2-nitrophenylsulfenyl)glycine dicyclohexylammonium salt and 140 mg of 4-N,N-dimethyl.aminopyridine hydrochloride were suspended in 25 ml of dichloromethane. After dissolution occurred, a solution of 273.3 mg of dicyclohexycarbodiimide in 5 ml of dichloromethane was added. The mixture was allowed to stand at ambient temperature overnight. The mixture was filtered and the filtrate was evaporated to dryness. The residue was flash chromatographed on silica gel in dichloromethane:methanol (10:0.2). The appropriate fractions were combined and evaporated to dryness The residue was crystallized from hexane:ether yielding, in two crops, 153.5 mg (30.1%) of product, mp 104° (dec).

ANALYSIS: Calculated for $C_{28}H_{38}N_2O_9S$: 58.11% C, 6.62% H, 4.84% N, Found: 57.63% C, 6.61% H, 5.41% N.

EXAMPLE 18

8,13-Epoxy-9α-hydroxy-1α-(t-butyldimethylsilyloxy)-labd-14-en-11-one 6β,7β-sulfite 8,13-Epoxy-6β,7β,9α-trihydroxy-1α-(t-butyldimethylsilyloxy)labd-14-en-11-one (200 mg) was dissolved in 2.0 ml of pyridine together with 200 ml of thionyl chloride at 5°. After 0.5 hr, the mixture was poured into water and extracted with ethyl acetate. The organic extracts were combined, dried over anhydrous sodium sulfate filtered and evaporated to dryness under vacuum. The residue was flash chromatographed (silica gel, hexane:ethyl acetate (3:1)). The appropriate fractions were combined and evaporated to dryness to give 122.2 mg of product, mp 107°–109°.

ANALYSIS: Calculated for $C_{26}H_{44}O_7SSi$: 59.05% C, 8.40% H, Found: 58.74% C, 8.24% H.

EXAMPLE 19

8,13-Epoxy-1α,9α-dihydroxylabd-14-en-11-one 6β,7β-sulfite 8,13-Epoxy-9α-hydroxy-1α-(t-butyldimethylsilyloxy)-labd14-en-11-one 6β,7β-sulfite (487.5 mg) was dissolved in 25 ml of acetonitrile and 40% aqueous hydrofluoric acid (95:5) and stirred at ambient temperature for six hrs. The mixture was basified with saturated aqueous sodium bicarbonate solution and the layers were separated. The aqueous phase was extracted with ethyl acetate which was then combined with the organic phase. The combined organic phases were dried over anhydrous sodium sulfate, filtered and evaporated to dryness. The residue was flash chromatographed on silica gel in hexane:ethyl acetate (3:1). The appropriate fractions were combined and evaporated to dryness to provide 208.7 mg (54.6%) of product, mp 186°–193° (dec).

ANALYSIS: Calculated for $C_{20}H_{30}O_7S$: 57.95% C, 7.31% H, Found: 58 27% C, 7.21% H.

EXAMPLE 20

8,13-Epoxy-1α,6β,9α-trihydroxy-7β-[2-(2-nitrophenylsulfenylamino)propionyloxy]labd-14-en-11-one 8,13-Epoxy-1α,6β,7β,9α-tetrahydroxylabd-14-en-11-one was dissolved in 50 ml of dry dichloromethane along with 863 mg of 2-(2-nitrophenylsulfenylamino)-propionic acid, dicyclohexylammonium salt, 323 mg of 4-dimethylaminopyridine hydrochloride and 547 mg of dicyclohexylcarbodiimide. The mixture was stirred at ambient temperature under nitrogen overnight, after which it was diluted with ether and filtered. The filtrate was evaporated and the residue was dissolved in dichloromethane and flash chromatographed on silica gel packed with dichloromethane:methanol (10:0.2). The appropriate fractions were combined and evaporated. The residue was crystallized from hexane:ether to give 627.6 mg (53%) of product, mp 209°–216°.

ANALYSIS: Calculated for $C_{29}H_{41}N_2O_9S$: 58 76% C, 6.82% H, 4 72% N, Found: 58 60% C, 7.06% H, 4 74% N.

EXAMPLE 21

8,13-Epoxy-1α,6β,9α-trihydroxy-7β-(2-tetrahydrofuranoyloxy)-labd-14-en-11-one 8,13-Epoxy-1,α,6β,7β,9α-tetrahydroxylabd-14-en-11-one (500 mg) was dissolved in 50 ml of dry dichloromethane along with 157.6 mg of 2-tetrahydrofuroic acid, 174 mg of 4-dimethylaminopyridine and 420 mg of dicyclohexylcarbodiimide. The mixture was stirred at ambient temperature under nitrogen overnight. The mixture was diluted with an equal volume of ether and was filtered. The filtrate was evaporated and the residue was flash chromatographed on silica gel in dichloromethane:methanol (10:0.2). The appropriate fractions were combined, evaporated, and the residue was crystallized from cyclohexane to give 180.5 mg (28.4%) of product, mp 162°–165°.

ANALYSIS: Calculated for $C_{25}H_{38}O_8$: 64.34% C, 8.23% H, Found: 64.25% C, 8.14% H.

EXAMPLE 22

7β-(1-Piperidinoacetosy)-8,13-epoxy-1α,6β,9α-trihydroxy and 14-en-11-one-1,9-dimethylformamide acetal 8,13-Epoxy-1α,6β,7β,9α-tetrahydroxylabd-14-en-11-one-1,9-dimethylformamide acetal (750 mg) was dissolved in 50 ml of dichloromethane with 318.3 mg of 2-(1-piperidino)acetic acid hydrochloride, 228 mg of 4-dimethylaminopyridine and 402 mg of dicyclohexylcarbodiimide. The mixture was stirred for 36 hrs at ambient temperature under nitrogen, diluted with an equal volume of ether and filtered. The filtrate was evaporated. The residue was flash chromatographed on silica gel in hexane:ethyl acetate (1:1), after which the appropriate fractions were combined and evaporated. The residue was crystallized from hexane to give 286.5 mg (29.6%) of product, mp 150°–155° (dec)

ANALYSIS: Calculated for $C_{30}H_{48}N_2O_7$: 65.65% C, 8.83% H, 5.10% N, Found: 65.68% C, 8.91% H, 5.22% N.

EXAMPLE 23

7β-(N,N-Dimethylaminoacetoxy)-8,13-epoxy-1α,6β,-9α-trihydroxylabd-14-en-11-one 1,9-dimethylformamide acetal 8,13-Epoxy-1α,6β,7β,9α-tetrahydroxylabd-14-en-11-one-1,9-dimethylformamide acetal (750 mg) was dissolved in 50 ml of dichloromethane and stirred at ambient temperature overnight, under nitrogen, along with N,N-dimethylglycine hydrochloride (247.5 mg), 4-dimethylaminopyridine (227.5 mg) and dicyclohexylcarbodiimide (402.4 mg). The mixture was diluted with an equal volume of ether, filtered and evaporated. The residue was flash chromatographed on silica gel in hexane:ethyl acetate:methanol (10:2:1). The appropriate fractions were combined and evaporated. The resultant oil was dried under vacuum at 20° to give 800 mg (89.0%) of product, mp 55°–60°.

ANALYSIS Calculated for $C_{27}H_{44}N_2O_7$: 63.73% C, 8.74% H, 5.50% N, Found: 63.56% C, 8.86% H, 5.33% N.

EXAMPLE 24

7β-(1-Piperidinoacetoxy)-8,13-epoxy-1α,6β,9α-trihydroxylabd-14-en-11-one hydrochloride hemietherate 7α-(1-Piperidinoacetoxy)-8,13-epoxy-1α,6β,9α-trihydroxylabd-14-en-11-one-1,9-dimethylformamide acetal (259.5 mg) was dissolved in 5 ml of methanol and 5 ml of 80% acetic acid. The mixture was stirred under nitrogen at ambient temperature overnight, evaporated, diluted with water, neutralized with sodium bicarbonate solution, and extracted with ether. The ether extracts were combined, dried over anhydrous sodium sulfate, filtered and evaporated. The residue was dissolved in anhydrous ether, from which the hydrochloride salt was precipitated by addition of ethereal hydrogen chloride. The precipitate was filtered, washed with anhydrous ether and dried under vacuum at 110° for 1 hr to afford 168.2 mg (62.6%) of product, mp 190°–194°.

ANALYSIS: Calculated for $C_{29}H_{49}ClNO_{7.5}$: 61.40% C, 8.72% H, 2.47% N, Found: 61.11% C, 8.88% H, 2.59% N.

EXAMPLE 25

1α-(N-t-Butylaminoacetoxy)-6β,9α-dihydroxy-8,13-epoxy-7β-(2-tetrahydrofuroyloxy)-labd-14-en-11-one hydrochloride hydrate 8,13-Epoxy-1α,6β,9α-trihydroxy-7β-(2-tetrahydrofuroyloxy)labd-14-en-11-one (200 mg) was dissolved in dry dichloromethane (2 ml) along with dimethylaniline (58.7 μl) with cooling to 5°. A solution of bromoacetyl bromide (49.1 μl) in dry dichloromethane (2 ml) was added dropwise over 0.5 hr to the solution. After 1 hr at 5°, the mixture was allowed to warm to ambient temperature and poured onto a mixture of ice and saturated aqueous sodium bicarbonate solution. The solution was extracted with ethyl acetate and the organic extract was dried over anhydrous sodium sulfate, filtered and evaporated. The residue was dissolved in dry dichloromethane (1 ml) and stirred under nitrogen. A solution of t-butylamine (91.2 μl) in ethyl acetate (2 ml) was added. The mixture was stirred at ambient temperature overnight, diluted with dichloromethane (10 ml) and washed with water followed by saturated aqueous sodium bicarbonate solution. The dichloromethane layer was evaporated and the residue was flash chromatographed on silica gel in hexane:ethyl acetate:methanol (10:10:0.01). The appropriate fractions were combined and evaporated. The residue was dissolved in anhydrous ether and treated with ethereal hydrogen chloride. The precipitate was filtered, washed with ether and dried under vacuum to give 1.22 mg (44.8%) of product, mp 165°-170°.

ANALYSIS: Calculated for $C_{31}H_{49}NO_9 \cdot HCl \cdot H_2O$: 58.70% C, 8.28% H, 2.21% N, Found: 58.96% C, 8.02% H, 2.12% N.

EXAMPLE 26

6β,9α-Dihydroxy-8,13-epoxy-1α-(N-2-propylaminoacetoxy)-7β-(2-tetrahydrofuroyloxy)labd-14-en-11-one hydrochloride hydrate 8,13-Epoxy-7β-(2-tetrahydrofuroyloxy)-1α,6β,9β,9α-trihydroxylabd-14-en-11-one (400 mg) was combined with N,N-dimethylaniline (117.4 μl) in dry dichloromethane (4 ml) at 5° C. under nitrogen. A solution of bromoacetyl bromide (98.2 μl) in dry dichloromethane (4 ml) was added and the mixture was stirred at that temperature for 2 hr. The mixture was allowed to warm to ambient temperature and was quenched with ice/water. The mixture was extracted into ethyl acetate and the organic phase washed with dilute aqueous sodium bicarbonate solution, dried over anhydrous sodium sulfate, filtered and evaporated. The residue was dissolved in dry dichloromethane (2 ml). One ml of the resultant mixture was added to a solution of 2-propylamine (146.2 μl) in ethyl acetate (1 ml). The mixture was stirred under nitrogen at ambient temperature overnight. The mixture was washed with 1 ml of saturated aqueous sodium bicarbonate solution, the layers were separated, and the organic phase was flash chromatographed on silica/gel in hexane:ethyl acetate:methanol (10:10:0.1). The appropriate fractions were combined and evaporated. The residue was dissolved in anhydrous ether and treated with ethereal hydrogen chloride to provide 100 mg (37.5%) of product, mp 144°-155°.

ANALYSIS: Calculated for $C_{30}H_{50}ClNO_{10}$: 58.09% C, 8.14% H, 2.26% N, Found: 58.29% C, 8.03% H, 2.25% N.

EXAMPLE 27

6β,9α-Dihydroxy-8,13-epoxy-1α-(4-morpholinoacetoxy)-7β-(2-tetrahydrofuroyloxy)labd-14-en-11-one hydrochloride hemihydrate 8,13-Epoxy-1α,6β,9α-trihydroxy-7β-(2-tetrahydrofuroyloxy)labd-14-en-11-one (400 mg) was combined with N,N-dimethylaniline (117.4 μl) in dry dichloromethane (4 ml) at 5° under nitrogen. A soultin of bromoacetyl bromide (98.2 μl) in dry dichloromethane (4 ml) was added and the mixture was stirred at 5° for 2 hr. The mixture was allowed to warm to ambient temperature, quenched with ice/water, and extracted into ethyl acetate. The organic phase was washed with dilute aqueous sodium bicarbonate solution and dried over anhydrous sodium sulfate, filtered and evaporated. The residue was dissolved in dry dichloromethane (2 ml). One ml of the resultant mixture was added to a solution of morpholine (149.8 μl) in ethyl acetate (1 ml). The mixture was stirred under nitrogen at ambient temperature overnight. The mixture was extracted with saturated aqueous sodium bicarbonate solution (1 ml). The organic phase was flash chromatographed on silca gel in hexane:ethyl acetate (1:1). The appropriate fractions were combined and evaporated. The residue was dissolved in anhydrous ether and treated with ethereal hydrogen chloride to provide 110 mg (40.1%) of product, mp 150°-154°.

ANALYSIS: Calculated for $C_{31}H_{49}ClNO_{10.5}$: 58.24% C, 7.74% H, 2.19% N, Found: 58.54% C, 7.76% H, 2.17% N.

EXAMPLE 28

8,13-Epoxy-7β-(2-methyltetrahydrofuro-2-yloxy)-1α,6β,9α-trihydroxy-labd-14-en-11-one 8,13-Epoxy-1α,6β,7β,9α-tetahydroxylabd-14-en-11-one (500 mg) was combined with 4-dimethylaminopyridine (174.3 mg), 2-methyl-2-tetrahydrofuroic acid (179.2 mg) and dicyclohexylcarbodiimide (308.3 mg) in dichloromethane (50 ml). The mixture was stirred at ambient temperature overnight under nitrogen. The mixture was diluted with an equal volume of ether, filtered and evaporated. The residue was flash chromatographed on silica gel in dichloromethane:methanol (10:0.4). The appropriate fractions were combined, evaporated and the residue was crystallized from cyclohexane:ether to yield 354.6 mg (52.8%) of product, mp 154°-164°.

ANALYSIS: Calculated for $C_{26}H_{40}O_8$: 64.96% C, 8.41% H, Found: 65.04% C, 8.40% N.

EXAMPLE 29

1α-(N-t-Butylaminoacetoxy)-6β,9α-dihydroxy-8,13-epoxy-7β-(2-methyltetrahydrofuro-2-yloxy)labd-14-en-11-one hydrochloride hydrate 8,13-Epoxy-1α,6β,9α-trihydroxy-7β-(2-methyltetrahydrofur-2-oyloxy)labd-14-en-11-one (164.0 mg) was dissolved in dichloromethane (2 ml) with N,N-dimethylaniline (44.3 mg) at 0°. A solution of bromoacetyl bromide (83.4 mg) in dichloromethane (2 ml) was added dropwise over 15 min. The mixture was stirred for 2 hr with gradual warming to room temperature. The mixture was partitioned between water and ethyl acetate. The organic layer was washed with saturated aqueous sodium bicarbonate solution, dried over anhydrous sodium sulfate, filtered and evaporated. The residue was dissolved in dichloromethane (1 ml) and stirred with a solution of t-butyl amine (100 mg) in ethyl acetate (2 ml) under nitrogen. The mixture was stirred at ambient temperature overnight, diluted with dichloromethane and washed with saturated aqueous sodium bicarbonate solution. The organic layer was separated and evaporated. The residue was flash chromatographed on silica gel in hexane:ethyl acetate:methanol (10:10:0.1). The appropriate fractions were combined and evaporated. The residue was dissolved in anhydrous ether and treated with ethereal hydrogen chloride to afford 65 mg (29.3%) of product, mp 156°–161°.

ANALYSIS: Calculated for $C_{32}H_{54}ClNIO_{10}$: 59.28% C, 8.41% H, 2.16% N, Found: 59.40% C, 8.41% H, 2.70% N.

EXAMPLE 30

7β-(2,2-Dimethyl-1,3-dioxolano-4-yloxy)-8,13-epoxy-1α,6β,9α-trihydroxylabd-14-en-11-one 8,13-Epoxy-1α,6β,7β,9α-tetrahydroxylabd- 14-en-11-one (500 mg) was dissolved in dichloromethane (50 ml) and stirred with 2,2-dimethyl-1,3-dioxolane-4-carboxylic acid potassium salt (250 mg), 4-dimethylaminopyridine hydrochloride (215.6 mg) and dicyclohexylcarbodiimide (294.3 mg) overnight, at ambient temperture under nitrogen. The mixture was diluted with an equal volume of ether and filtered. The filtrate was evaporated. The residue was flash chromatographed on silica gel in hexane:ethyl acetate (3:1). The appropriate fractions were combined and evaporated to afford 350.8 mg (50.5%) of product, mp 100° (softening).

ANALYSIS: Calculated for $C_{26}H_{40}O_9$: 62.87% C, 8.13% H, Found: 63.17% C, 8.59% H.

EXAMPLE 31

7β-(2,3-Dihydroxypropionyloxy)-8,13-epoxy-1α,6β,-9α-trihydroxy-labd-14-en-11-one 8,13-Epoxy-7β-(2,2-dimethyl-1,3-dioxolano-4-yloxy)-1α,6β,9α-trihydroxylabd-14-en-11-one (204 mg) was dissolved in a mixture of 80% acetic acid (2 ml) and methanol (0.4 ml), under nitrogen, and the mixture was stirred at ambient temperature for 3 days. The mixture was evaporated. The residue was flash chromatographed on silica gel in hexane:ethyl acetate:methanol (10:10:0.01). The appropriate fractions were combined and evaporated. The residue was crystallized from cyclohexane:ether to afford 85.0 mg (45.3%) of product, mp 162°–178°.

ANALYSIS: Calculated for $C_{23}H_{36}O_9$: 60.50% C, 7.96% H, Found: 60.46% C, 8 05% H.

EXAMPLE 32

1α-(N-t-Butylaminoacetoxy)-6β,9α-dihydroxy-7β-(2,2-dimethyl-1,3-dioxolano-4-yloxy)-8,11-epoxylabd-14-en-11-one hydrochloride hydrate 7β-(2,2-Dimethyl-1,3-dioxolano-4-yloxy)-8,13-epoxy-1α,6β,9α-trihydroxylabd-14-en-11-one (500 mg) was dissolved in dry dichloromethane (6 ml) with N,N-dimethylaniline (137.6 µl) under nitrogen. The mixture was cooled to 5°. Bromoacetyl bromide (105.6 µl) dissolved in dry dichloromethane (6 ml) was added to the stirred solution and the mixture was allowed to stand for 2 hr with gradual warming to ambient temperature. The mixture was partitioned between ether and water. The organic phase was separated, washed with saturate,d aqueous sodium bicarbonate solution, dried over anhydrous sodium sulfate, filtered, and evaporated. The residue was dissolved in dichloromethane (5 ml) and stirred under nitrogen with t-butylamine (214.3 ml) dissolved in 10 ml of ethyl acetate. The mixture was allowed to stand at ambient temperature overnight. The mixture was partitioned between ethyl acetate and saturated aqueous sodium bicarbonate solution. The organic layer was evaporated. The residue was flash chromatographed on silica gel in hexane:ethyl acetate:methanol (10:10:0.1). The appropriate fractions were combined and evaporated. The residue was dissolved in ether and treated with ethereal hydrogen chloride to afford 303.1 mg (45 2%) of product, mp 170°–176° (dec).

ANALYSIS:
Calculated for $C_{32}H_{54}ClNO_{11}$: 57.85% C, 8.21% H, 2.11% N, Found: 58.05% C, 8.02% H, 2.00% N.

EXAMPLE 33

8,11-Epoxy-7β-(pyroglutamoyloxy)-1α,6β,9α-trihydroxylabd-14-en-11-one 8,11-Epoxy-1α,6β,7β,9α-tetrahydroxylabd-14-en-11-one (500 mg) was dissolved in dichloromethane (50 ml) and stirred together with pyroglutamic acid (175.3 mg), 4-dimethylaminopyridine (174.3 mg) and dicyclohexylcarbodiimide (308.3 mg) overnight at ambient temperature, under nitrogen. The mixture was diluted with an equal volume of ether and filtered. The filtrate was evaporated. The residue was flash chromatographed on silica gel in hexane:ethyl acetate:methanol (10:10:1). The appropriate fraction,s were combined and evaporated. The residue was dissolved in ether and precipitated with hexane to afford 266.9 mg (41.0%) of product, mp 150°–160°.

ANAYSIS: Calculated for $C_{25}H_{37}NO_8$: 62.60% C, 7.79% H, 2.92% N, Found: 62.94% C, 7.945 H, 2.66% N.

EXAMPLE 34

8,13-Epoxy-7β-[N-(2-nitrophenylsulfenyl)prolyloxy]-1α,6β,9α- trihydroxylabd-14-en-11-one 8,13-Epoxy-1α,6β,7β,9α-tetrahydrolabd-14-en-11-one (750 mg) was combined with 4-(N,N-dimethylamino)pyridine hydrochloride (323 mg), N-(2-nitrophenylsulfenyl)proline dicyclohexyl ammonium salt (917.2 mg) and dicyclohexylcarbodiimide (505.0 mg) in dichloromethane (50 ml). The mixture was stirred at ambient temperature under nitrogen overnight. The mixture was diluted with an equal volume of ether, filtered and evaporated. The residue was flash chromatographed on silica gel in dichloromethane:methanol (10:0.2). The appropriate fractions were combined and evaporated to dryness. The residue was crystallized from hexane:ether to afford 880.3 mg of product, mp 125°–129°.

ANALYSIS: Calculated for $C_{31}H_{42}N_2O_9S$: 60.17% C, 6.86% H, 4.52% N, Found: 60.69% C, 7.09% H, 4.53% N.

EXAMPLE 35

8,13-Epoxy-1α,6β, 9α-trihydroxy-7β-prolyloxylabd-14-en-11-one 8,13-Epoxy-7β-[N-(2-nitrophenylsulfenyl)prolyloxy)-1α,6β, 9α-tribhydroxylabd-14-en-11-one (480 mg) was dissolved in either (20 ml). Saturated ethereal hydrogen chloride (2 ml) was added and the mixture was stirred for 15 min. The precipitate ws filtered, washed with either and dried at 80° to yield 125 mg (31.0%) of product, mg 180°–195°.

ANALYSIS: Calculated for $C_{25}H_{42}ClNO_8$: 57.73% C, 8.16% H, 2.69% N, Found: 58.16% C, 7.89% H, 3.24% N.

EXAMPLE 36

8,13-Epoxy-6-(2-tetrahydrofuroyloxy)-1α,7β, 9α-trihydroxylabd-14-en-11-one 8,13-Epoxy-7β-(2-tetrahydrofuroyloxy)-1α,6β,9α-trihydroxylabd-14-en-11one (200 mg) was dissolved in dry tetrahydrofuran (5 ml) and maintained at −78°. Lithium bis(trimethylsilyl)amide (492.2 μl, 1M in tetrahydrofuran) was added and the mixture was warmed to 0°. The mixture was stirred for 3 hr after whch additional lithium bis(trimethylsilyl)amide (200 μl, 1M in tetrahydrofuran) was added. After a total time of 6 hr, the reaction was flash chromatographed on silica gelin hexane:ethyl acetate: methanol (2:1:0.01) to afford 68.0 mg (34.0%) of product, mp 100°–115°.

ANALYSIS: Calculated for $C_{25}H_{38}O_8$: 64.34% C, 8.23% H, Found: 64.02% C, 8.16% H.

EXAMPLE 37

1α-(N-t-Butylaminoacetoxy)-7β,9α-dihydroxy-8,13-epoxy-6β-(2-tetrahydrofuroyloxy)labd-14-en-11-one To a stirred solution of 8,13-epoxy-6β-(tetrahydrofurano-2-yloxy)-1α,7β,9α-trihydroxylabd-14-en-11-one (300 mg) in dry dichloromethane (3 ml) containing N,N-dimethylaniline (0.11 ml) in an ice bath, under nitrogen, was added dropwise a solution of bromoacetyl bromide (0.075 ml) in dichloromethane (6 ml). The solution was stirred at 0° for 1 hr. The solution was poured into ice/water/ethyl acetate, extracted with ethyl acetate, washed with cold sodium bicarbonate solution, water and dried over anhydrous sodium sulfate. Filtration followed by evaporation of solvent provided an oil which was dissolved in dichloromethane (3 ml) and added to a solution of t-butylamine (0.3 g) in ethyl acetate (3 ml). The mixture was stirred overnight, poured into ice/water/ethyl acetate. The layers were separated and the organic phase was washed twice with water, saturated sodium chloride solution and dried over anhydrous sodium sulfate. Filtration followed by evaporation of solvent provided an oil. The oil was dissolved in ether and treated with ethereal hydrogen chloride to provide 169 mg (41.4%) of product, mp 165°–176°.

ANALYSIS: Calculated for $C_{31}H_{49}NO_9.HCl.H_2O$: 58.71% C, 8.26% H, 2.21% N, Found: 58 47% C, 8.01% H, 2.13% N.

EXAMPLE 38

8,13-Epoxy-6β-(2,2-dimethyl-1,3-dioxolano-4-yloxy)-1α,7β,9α-trihydroxylabd-14-en-11-one 8,13-Epoxy-7β-(2,2-dimethyl-1,3-dioxolano-4-yloxy)-1α,6β,9α-trihydroxylabd-14-en-11-one (1.4 g) was dissolved in dry tetrahydrofuran (30 ml) under nitrogen and cooled to 5°. Lithium bis(trimethylsilyl)amide (2.82 ml, 1M in tetrahydrofuran) was added, with stirring. The mixture was allowed to stand for 2 hr at 5° C. The product was partitioned between saturated aqueous sodium bicarbonate solution and ethyl acetate. The organic layer was separated, dried over anhydrous sodium sulfate, filtered and evaporated. The residue was dissolved in hexane:ethylacetate (3:1) and flash chromatographed on silica gel eluting with 800 ml of hexane:ethyl acetate (3:1) followed by 900 ml of hexane:ethyl acetate (2:1). The appropriate fractions were ccmbined and evaporated. The residue was crystallized from hexane:ethyl acetate to provide 470 mg (33.6%) of product, mp 110°–120°.

ANALYSIS: Calculated for $C_{26}H_{40}O_9$: 62.87% C, 8.13% H, Found: 63.25% C, 8.28% H.

EXAMPLE 39

8,13-Epoxy-6β-(2,3-dihydroxypropionyloxy)-1α,7,β, 9α-trihydroxy-labd-14-en-11-one 8,13-Epoxy-6β-(2,2-dimethyl-1,3-dioxolano-4-yloxy)-1α,7β,9α-trihydroxylabd-14-en-11-one (390 mg) was dissolved in 80% acetic acid (4.5 ml) and stirred with methanol (4.5 ml) at 50° for 2 days, under nitrogen. The solvent was evaporated and the residue was partitioned between chloroform and saturated sodium bicarbonate solution. The chloroform extracts were combined, dried over anhydrous sodium sulfate, filtered and evaporated. The residue was flash chromatographed on silica gel in dichloromethane:methanol (19:1). The appropriate. fractions were combined, evaporated and the residue was dried under vacuum at 100° vernight to afford 91 mg (25.3%) of product, mp 225°–235°.

ANALYSIS: Calculated for $C_{23}H_{36}O_9$: 60.50% C, 7.96% H, Found: 59.07% C, 7.88% H.

EXAMPLE 40

8,13-Expoxy-1α,6β,7β,9α-tetrahydroxylabd-14-en-11-one-6,7-carbonate 1,9-dimethylformamide acetal 8,13-Epoxy-1α,6β,7β,9α-tetrahydroxylabd-14-en-11-one 1,9-dimethylformamide acetal (1.059 g) was heated under reflux in toluene (25 ml) containing N,N'-carbonyldiimidazole (0.50 g) and triethylamine (0.55 ml). After 3 hr, the reaction mixture was evaporated and the residue was applied directly to a flash chromatograph. Elution with 50% ethyl acetate-hexane gave 0.976 g (87%) of product after combination of the appropriate fractions. The analytical sample obtained by recrystallization from hexane had mp 138°–140°.

ANALYSIS: Calculated for $C_{24}H_{25}NO_7$: 64.12% C, 7.85% H, 3.12% N, Found: 63.91% C, 7.98% H, 3.08% N.

EXAMPLE 41

8,13-Epoxy-6β-methoxyacetoxy-1α,7β,9α-trihydroxylabd-14-en-11-one

To a stirred solution of 0.317 g of 8,13-epoxy-7β-methoxyacetoxy-1α,6β,9α-labd-14-en-11-one in tetrahydrofuran (75 ml) was added 1M lithium bis(trimethylsilyl)amide in hexanes (1.36 ml) in an ice bath. The solution was stirred 1 hr at 0°, poured into ice/water and extracted with ethyl acetete. The organic extracts were washed three times with water, once with saturated sodium chloride solution and dried over anhydrous sodium sulfate. Filtration followed by evaporation of solvent provided an oil. The oil was dissolved in a minimum volume of 35% ethyl acetate/hexane and flash chromatographed on 200 g of silica gel. Evaporation of solvent from the apprcpriate fractions provided 0.147 g (46.4%) of product, mp 164°–165°.

ANALYSIS: Calculated for $C_{23}H_{36}O_8$: 62.71% C, 8.24% H, Found: 62.58% C, 8.32% H.

EXAMPLE 42

7β-(1,2:3,4-Diisopropylidine-D-galacturonoyloxy)-8,13-epoxy-1α,6β,9α-trihydroxylabd-14-en-11-one 8,13-Epoxy-1α,6β,7β,9α-trihydroxylabd-14-en-11-one (500 mg), 1,2:3,4-diisopropylidine galacturonic acid (410 mg), 4-dimethylaminopyridine (180 mg) and dicyclohexylcarbodiimide (35 mg) were dissolved in dichloromethane (50 ml) and stirred under nitrogen at ambient temperature overnight. The mixture was filtered and evaporated. The residue was triturated with ethyl acetate and filtered. The filtrate was evaporated and the residue was flash chromatographed on silica gel in dichloromethane:methanol (98:2). The appropriate fractions were combined and evaporated. The residue was crystallized from hexane:ether to afford 209 mg (24.6%) of product, mp 229°–233°.

ANALYSIS: Calculated for $C_{32}H_{48}O_{12}$: 61.51% C, 7.76% N, Found: 60.96% C, 7.78% H.

EXAMPLE 43

7β-[3-(Demethylphosphinyl)propionyloxy]-8,13-epoxy-1α,6β,9α-trihydroxylabd-14-en-11-one A solution of 8,13-epoxy-1α,6β,7β,9α-tetrahydroxylabd-14-en-11-one (600 mg), 2-carboxyethyldimethylphosphine oxide (300 mg), dimethylaminopyridine (20 mg), dicyclohexylcarbodiimide (440 mg) and dichloromethane (60 ml) was stirred at room temperature for 16 hrs. The suspension was filtered and flash chromatographed (without being concentrated) on silica gel (eluent: 4% methanol/dichloromethane). Concentration of the appropriate fractions provided 0.559 g (68.7%) of product, mp 252°–259°.

ANALYSIS: Calculated for $C_{25}H_{41}O_8P$: 59.98% C, 8.26% H, Found: 59.32% C, 8.81% H.

EXAMPLE 44

8,13-Epoxy-7β-[2-(methoxyethoxymethoxy)-2-methylpropionyloxy]-1α,6β,9α-trihydroxylabd-14-en-11-one To a stirred solution of 8,13-epoxy-1α,6β,7β,9α-tetrahydroxylabd-14-en-11-one (0.5 g) in 50 ml of dry dichloromethane was added 2-hydroxyisobutyric acid methoxyethoxyethyl ether (0.313 g), 1-(3-dimethylaminopropyl)-3-ethylcarbodiimide hydrochloride (0.313 g) and 4-dimethylaminopyridine (0.166 g). The reaction mixture was stirred at room temperature for 48 hrs, under nitrogen. The mixture was diluted with ether, washed three times with water, once with saturated sodium chloride solution, dried over anhydrous sodium sulfate and filtered. The filtrate was evaporated and the residue was dissolved in a minimum volume of 20% butyl acetate/hexane and flash chromatographed on silica gel, eluting with 10×200 ml of 20% n-butyl acetate/hexanes, 10×200 ml of 25% n-butyl acetate/hexanes, 10×200 ml of 30% n-butyl acetate/hexanes, 10×200 ml of 40% n-butyl acetate/hexanes and 10×200 ml of 50% n-butyl acetate/hexanes. Concentration of the appropriate fractions provided an oil, which crystallized on standing. Recrystallization from cyclohexane/ethyl acetate provided 96 mg (10.9%) of product, mp 144°.

EXAMPLE 45

8,13-Epoxy-7β-(2-methoxy-2-methylpropionyloxy)-1α,6β,9α-trihydroxylabd-14-en-11-one A solution of 8,13-epoxy-1α,6β,7β,9α-tetrahydroxylabd-14-en-11-one (0.5 g), dichloromethane (50 ml), 2-methoxy-2-methylpropionic acid (0.175 g), dimethylaminopyridine (0.171 g), and 1-(3-dimethylaminopropyl)-3-ethylcarbodiimide hydrochloride (0.263 g) was stirred at room temperature for 5 days. The reaction mixture was diluted with ether, washed three times with water, once with saturated sodium chloride solution, dried over anhydrous sodium sulfate and filtered. The filtrate was evaporated. The residue was flash chromatographed on silica gel (eluent: 25% ethyl acetate/hexane). The appropriate fractions were evaporated. The residue was recrystallized from cyclohexane/ethyl acetate to provide 53 mg (8.4% of product, mp 140°–142°.

ANALYSIS: Calculated for $C_{25}H_{40}O_8$: 64.08% C, 8.60% H, Found: 64.20% C, 8.66% H.

EXAMPLE 46

8,13-Epoxy-7β-(2-methoxy-2-methylpropionyloxy)-1α,6β,9α-trihydroxylabd-14-en-11-one 1,9-carbonate A solution of 8,13-epoxy-1α,6β,7β9α-tetrahydroxylabd-14-en-11-one (2.0 g), dicyclohexylcarbodiimide (1.4 g), 2-methoxy-2-methylpropionic acid (0.7 g), 4-dimethylaminopyridine (0.684 g) and dichloromethane (200 ml) was stirred at room temperature overnight. To the suspension was added 100 ml of anhydrous ether. The solution was stirred for an additional 10 mins and filtered. The filtrate was washed three times with water, once with saturated sodium chloride solution and dried over anhydrous sodium sulfate. The mixture was filtered and the filtrate was evaporated. The residue was triturated with ethyl acetate and filtered. The filtrate was concentrated to an oil, the residue was dissolved in a minimum volume of 25% ethyl acetate/hexane and flash chromatographed on 500 g of silica gel. The appropriate fractions were combined and concentrated. To a solution of the residue in 50 ml of pyridine cooled in an ice-bath, under nitrogen, was added dropwise a solution of 12.5% phosgene in toluene (5 ml). The mixture was stirred for 45 min at ice bath temperature and 1 hr at room temperature. The mixture was poured into ice water/ethyl acetate, washed three times with water, once with saturated sodium chloride solution, dried over anhydrous sodium sulfate and filtered. The filtrate was evaporated. The residue was dissolved in a minimum volume of 25% ethyl acetate/hexane and flash chromatographed on 500 g of silica gel. The appropriate fractions were combined and concentrated. The residue, which crystallized on standing, was recrystallized from cyclohexane/ethyl acetate to provide 600 mg (22.3%) of product, mp 135°–138°.

ANALYSIS: Calculated for $C_{26}H_{38}O_9$: 63.14% C, 7.74% H, Found: 63.04% C, 7.74% H.

EXAMPLE 47

8,13-Epoxy-7β-(3-furoyloxy)-1α,6β,9α-trihydroxylabd-14-en-11-one hemihydrate 8,13-epoxy-1α,6β,7β,9α-tetrahydroxylabd-14-en-11-one (500 mg) was combined with 4-dimethylaminopyridine (174.3 mg), 3-furoic acid (152.2 mg) and dicyclohexylcarbodiimide (308.3 mg) in 50 ml of dichloromethane under nitrogen. The mixture was stirred overnight at ambient temperature. The mixture was diluted with an equal volume of ether, filtered, and evaporated to dryness. The residue was flash chromatographed on silica gel in hexane:ethyl acetate (3:1). The appropriate fractions were combined, evaporated and crystallized from cyclohexane:ether to afford 232.4 mg (35.2%) of product, mp 241°-244°.

ANALYSIS: Calculated for $C_{25}H_{35}O_{8.5}$: 63.67% C, 7.50% H, Found: 63.48% C, 7.27% H.

EXAMPLE 48

8,13-Epoxy-7β-(2-furoyloxy)-1α,6β,9α-trihydroxylabd-14-en-11-one 8,13-epoxy-1α,6β,7β,9α-tetrahydroxylabd-14-en-11-one (500 mg) was combined with 174.3 mg of 4-dimethylaminopyridine, 2-furoic acid (152.2 mg) and dicyclohexylcarbodiimide (308.3 mg) in 50 ml of dichloromethane under nitrogen. The mixture was allowed to stir at ambient temperature overnight. The mixture was diluted with an equal volume of ether, filtered and evaporated. The residue was flash chromatographed on silica gel in hexane:ethyl acetate (3:1). The appropriate fractions were combined and evaporated. The residue was crystallized from cyclohexane:ether to afford 265.3 mg (41.0%) of product, mp 241°-245°.

ANALYSIS Calculated for $C_{25}H_{34}O_8$: 64.91% C, 7.42% H, Found: 64.88% C, 7.25% H.

EXAMPLE 49

6β-(N-Acetylaminoacetoxy)-8,13-epoxy-1α,7β,9α-trihydroxylabd-14-en-11-one

7β-(N-Acetylaminoacetoxy)-8,13-epoxy-1α,6β,9α-trihydroxylabd-14-en-11-one (630.2 mg) was dissolved in 50 ml of tetrahydrofuran under nitrogen. The solution was cooled to 0°, and after 15 min, lithium bis(trimethylsilyl)amide (2.7 ml of 1M tetrahydrofuran solution) was added, followed by stirring for 2 hr at 0°. The reaction mixture was quenched with 100 ml water, after which the solvent was removed by evaporation. The residue was flash chromatographed on silica gel in hexane:ethyl acetate:methanol (10:10:1). The appropriate fractions were combined and evaporated. The residue was crystallized from hexane:ethyl acetate affording 177.8 mg (28.2%) of product, mp 130°-150°.

ANALYSIS: Calculated for $C_{24}H_{37}NO_8$: 61.64% C, 7.99% H, 2.99% N, Found: 61.43% C, 7.99% H, 2.82% N.

EXAMPLE 50

8,13-Epoxy-7β-(2-hydroxy-2-methylpropionyloxy)-1α,6β,9α-trihydroxylabd-14-en-11-one A solution of 8,13-epoxy-7β-(2-methoxyethoxymethoxy-2-methylpropionyloxy)-1α,6β,9α-trihydroxylabd-14-en-11-one (100 mg) in 3:1:1-glacial acetic acid:methanol:water was stirred in a sealed tube at 90° for 20 hrs. The reaction mixture was allowed to cool to ambient temperature, and ether and ice water were added. The solution was extracted twice with ether, and the ethereal extracts were washed three times with water, once with saturated sodium chloride solution, dried over anhydrous sodium sulfate and filtered. The filtrate was evaporated. The residue was dissolved in 30% n-butyl acetate/hexanes and flashed chromatographed on silica gel (100 g), eluting with 30% n-butyl acetate/hexanes followed by 40% n-butyl acetate/hexanes. Concentration of the appropriate fractions provided 12.0 mg. (14.2%) of product as an amorphous solid, mp 155°-177°.

ANALYSIS:

Calculated for $C_{24}H_{34}O_8$: 63.41% C, 8.43% H, Found: 63.23% C, 8.44% H.

REACTION SCHEME A

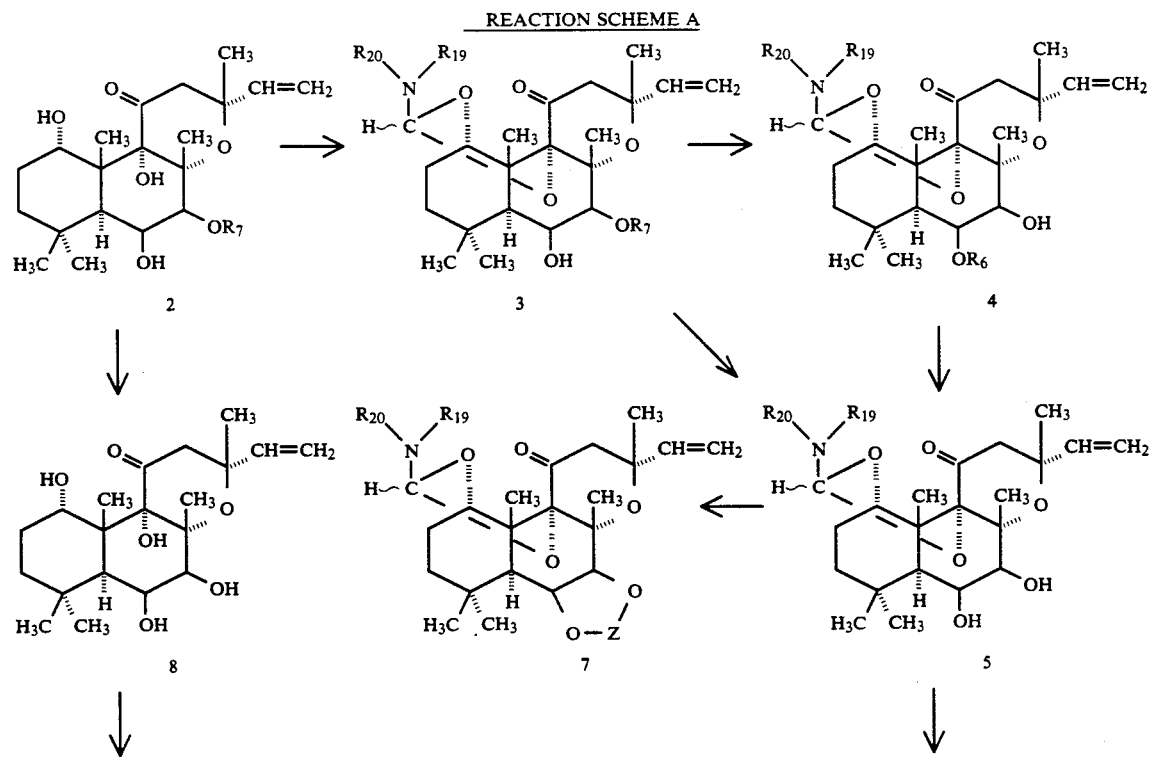

-continued
REACTION SCHEME A
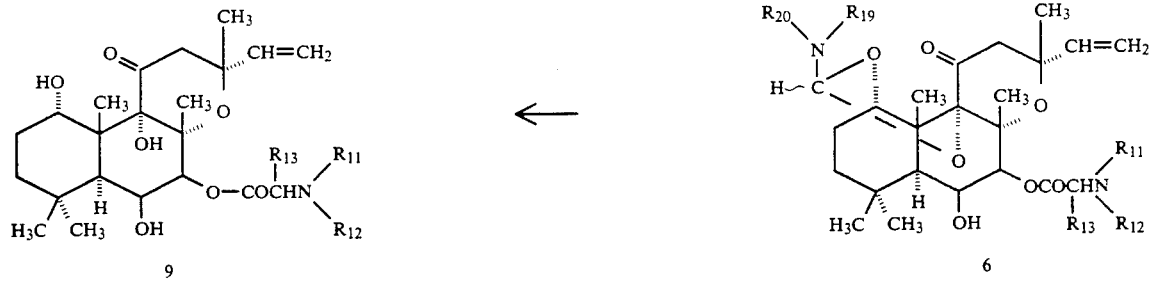
wherein $R_6$, $R_7$, $R_{11}$, $R_{12}$, $R_{13}$, $R_{19}$, $R_{20}$ and Z are as hereinbeforedescribed.
REACTION SCHEME B
REACTION SCHEME C
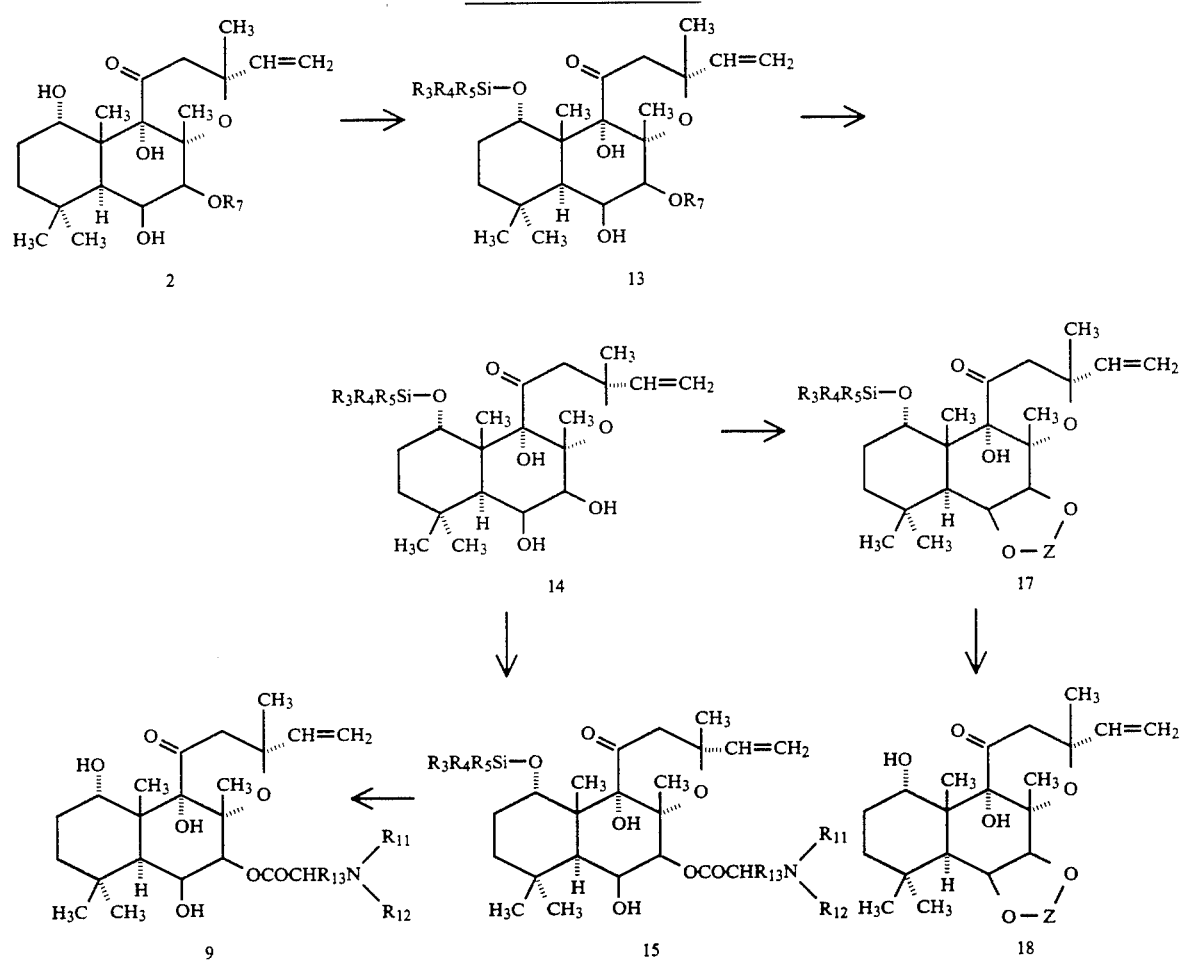
wherein $R_3$, $R_4$, $R_5$, $R_7$, $R_{11}$, $R_{12}$, $R_{13}$, and Z are as hereinbeforedescribed.

-continued
REACTION SCHEME C

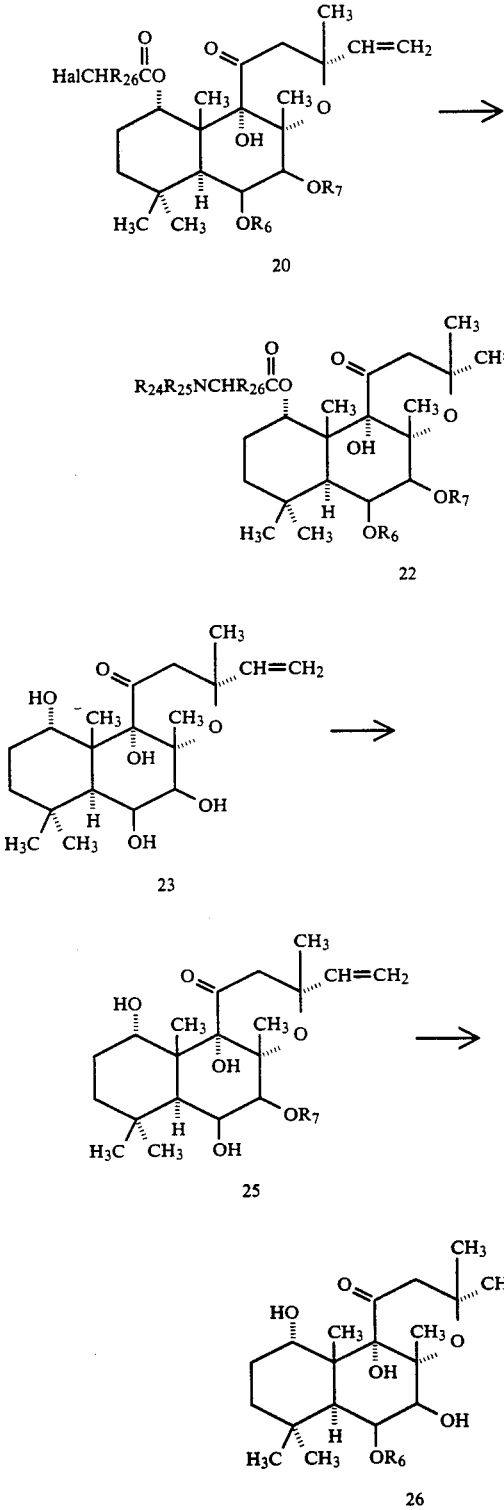

wherein $R_6$, $R_7$, $R_{24}$, $R_{25}$, $R_{26}$ and Hal are as hereinbeforedescribed.

We claim:

1. A process for the preparation of a compound of the formula

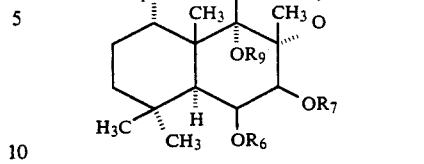

wherein:
(a) $R_1$ is hydrogen;
(b) $R_6$ is a group of the formula $R_8CO$ wherein $R_8$ is hydrogen, loweralkyl,

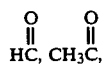

$CH_3CHOH$, $HOCH_2CHOH$, $CH_3C(CH_3)OH$, $(CH_3)_2COCH_2OCH_2CH_2OCH_3$, $CH_3C(CH_2OH)_2$, $C(CH_2OH)_3$,

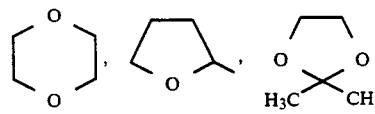

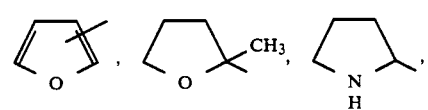

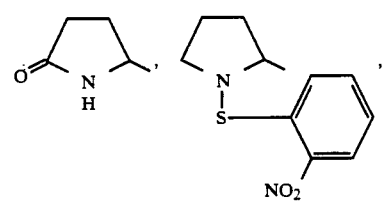

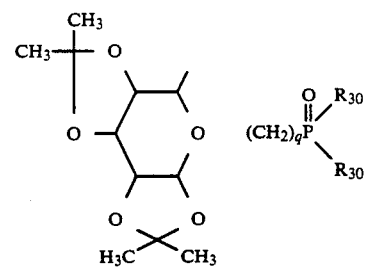

wherien $R_{30}$ is loweralkyl and q is 1, 2 or 3, a group of the formula $R_{10}OCR_{31}R_{32}(CH_2)_n$ wherein $R_{10}$ is loweralkyl, $R_{31}$ is hydrogen or loweralkyl, $R_{32}$ is hydrogen or loweralkyl, and n is 0, 1, 2 or 3; and $R_7$ is hydrogen;
(c) $R_9$ is hydrogen; and
(d) $R_1$ and $R_9$ taken together form a group of the formula CO, a group of the formula SO or a group of the formula $CHNR_{19}R_{20}$ wherein $R_{19}$ and $R_{20}$ are each independently loweralkyl; and $R_{19}$ and $R_{20}$ taken together with the nitrogen atom to which they are attached form a group of the formula

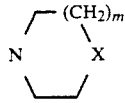

wherien X is O, S, a group of the formula $CHR_{15}$ wherein $R_{15}$ is hydrogen, loweralkyl or a group of the formula $OR_{16}$ wherein $R_{16}$ is loweralkyl, and m is 0 or 1; or a group of the formula $NR_{18}$ wherein $R_{18}$ is loweralkyl, which comprises contacting a compound of the formula

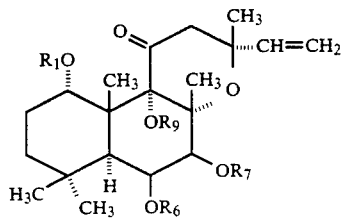

wherein:
(a) $R_1$ is hydrogen;
(b) $R_6$ is hydrogen;
(c) $R_7$ is a group of the formula $R_8CO$ wherein $R_8$ is as above and n are as above;

(d) $R_9$ is hydrogen; and
(e) $R_1$ and $R_9$ taken together form a group of the formula CO, a group of the formula SO or a group of the formula $CHNR_{19}R_{20}$ wherein $R_{19}$ and $R_{20}$ are as above; and $R_{19}$ and $R_{20}$ taken together with the nitrogen atom to which they are attached form a group of the formula

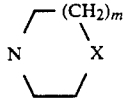

wherein X is O, S, a group of the formula $CHR_{15}$ wherein $R_{15}$ is as above, a group of the formula $OR_{16}$ wherein $R_{16}$ and m is as above, or a group of the formula $NR_{18}$ wherein $R_{18}$ is as above in the presence of an alkali metal bis(-triloweralkylsilyl)amide.

2. The process of claim 1 wherein the alkali metal bis(triloweralkylsilyl)amide is lithium bis(trimethylsilyl)amide.

3. The process of claim 1 wherein the reaction is conducted in a solvent.

4. The process of claim 3 wherein the solvent is an ethereal solvent.

5. The process of claim 4 wherein the ethereal solvent is tetrahydrofuran.

* * * * *